(12) United States Patent
Voytik-Harbin et al.

(10) Patent No.: US 12,708,696 B2
(45) Date of Patent: Aug. 18, 2026

(54) HIGH-STRENGTH COLLAGEN COMPOSITIONS AND METHODS OF USE

(71) Applicant: GENIPHYS, INC., Zionsville, IN (US)

(72) Inventors: Sherry L. Voytik-Harbin, Zionsville, IN (US); Theodore J. Puls, Carmel, IN (US)

(73) Assignee: GENIPHYS, INC., Zionsville, IN (US)

( * ) Notice: Subject to any disclaimer, the term of this patent is extended or adjusted under 35 U.S.C. 154(b) by 733 days.

(21) Appl. No.: 17/915,719

(22) PCT Filed: Mar. 30, 2021

(86) PCT No.: PCT/US2021/024893

§ 371 (c)(1),
(2) Date: Sep. 29, 2022

(87) PCT Pub. No.: WO2021/202533

PCT Pub. Date: Oct. 7, 2021

(65) Prior Publication Data

US 2023/0131204 A1 Apr. 27, 2023

Related U.S. Application Data

(60) Provisional application No. 63/002,644, filed on Mar. 31, 2020.

(51) Int. Cl.
*A61L 27/24* (2006.01)
*A61L 27/38* (2006.01)
*A61L 27/50* (2006.01)

(52) U.S. Cl.
CPC .......... *A61L 27/24* (2013.01); *A61L 27/3834* (2013.01); *A61L 27/50* (2013.01); *A61L 2430/20* (2013.01)

(58) Field of Classification Search
CPC ...... A61L 27/24; A61L 27/3834; A61L 27/50; A61L 2430/20; A61L 27/56; A61L 27/44; A61L 27/54
See application file for complete search history.

(56) References Cited

U.S. PATENT DOCUMENTS 3,949,073 A 4/1976 Daniels
4,233,360 A 11/1980 Luck
4,439,521 A 3/1984 Archer
(Continued)

FOREIGN PATENT DOCUMENTS

AU 4884199 A 3/2000
CN 1100446500 11/2019
(Continued)

OTHER PUBLICATIONS

PCT Search Report and Written Opinion prepared for PCT Application No. PCT/US2021/024893, completed May 27, 2021.
(Continued)

*Primary Examiner* — Yashita Sharma
(74) *Attorney, Agent, or Firm* — Barnes & Thornburg LLP

(57) ABSTRACT

The invention relates to engineered collagen scaffolds with a thickness of from about 0.005 mm to about 3 mm, and with a high strength (e.g., a high elastic modulus of from about 0.5 MPa to about 200 MPa). The engineered collagen scaffolds can be non-collapsible and/or non-expandable. This disclosure also relates to methods of use of these collagen scaffolds.

18 Claims, 10 Drawing Sheets

(56) References Cited

U.S. PATENT DOCUMENTS 4,544,516 A 10/1985 Hughes
4,582,640 A 4/1986 Smestad
4,600,533 A 7/1986 Chu
4,703,108 A 10/1987 Silver
4,743,552 A 5/1988 Friedman
4,776,853 A 10/1988 Klement
4,789,663 A 12/1988 Wallace
4,801,299 A 1/1989 Brendel
4,829,000 A 5/1989 Kleinman
4,902,508 A 2/1990 Badylak
4,912,057 A 3/1990 Guirguis
4,956,178 A 9/1990 Badylak
5,032,508 A 7/1991 Naughton
5,067,961 A 11/1991 Kelman
5,163,955 A 11/1992 Love
5,204,382 A 4/1993 Wallace
5,266,480 A 11/1993 Naughton
5,275,826 A 1/1994 Badylak
5,281,422 A 1/1994 Badylak
5,336,616 A 8/1994 Livesey
5,352,463 A 10/1994 Badylak
5,420,248 A 5/1995 Devictor
5,460,962 A 10/1995 Kemp
5,478,739 A 12/1995 Slivka
5,554,389 A 9/1996 Badylak
5,604,106 A 2/1997 Liotta
5,641,518 A 6/1997 Badylak
5,695,998 A 12/1997 Demeter
5,800,812 A 9/1998 Eisenbach-Schwartz
5,863,531 A 1/1999 Naughton
5,885,619 A 3/1999 Patel
5,948,429 A 9/1999 Bell
6,020,200 A 2/2000 Enevold
6,099,567 A 8/2000 Badylak
6,171,344 B1 1/2001 Atala
6,187,039 B1 2/2001 Hiles
6,187,047 B1 2/2001 Kwan
6,206,931 B1 3/2001 Cook
6,241,981 B1 6/2001 Cobb
6,248,587 B1 6/2001 Rodgers
6,264,992 B1 7/2001 Voytik-Harbin
6,375,989 B1 4/2002 Badylak
6,379,710 B1 4/2002 Badylak
6,384,196 B1 5/2002 Weis
6,419,920 B1 7/2002 Mineau-Hanschke
6,475,232 B1 11/2002 Babbs
6,485,723 B1 11/2002 Badylak
6,497,875 B1 12/2002 Sorrell
6,586,493 B1 7/2003 Massia
6,592,623 B1 7/2003 Bowlin
6,592,794 B1 7/2003 Bachrach
6,666,892 B2 12/2003 Hiles
6,682,670 B2 1/2004 Lullwitz
6,893,812 B2 5/2005 Woltering
6,918,396 B1 7/2005 Badylak
6,962,814 B2 11/2005 Mitchell
7,029,689 B2 4/2006 Berglund
7,087,089 B2 8/2006 Patel
7,338,517 B2 3/2008 Yost
7,795,022 B2 9/2010 Badylak
7,815,686 B2 10/2010 Badylak
8,084,055 B2 12/2011 Voytik-Harbin
8,222,031 B2 7/2012 Noll
8,241,905 B2 8/2012 Forgacs
8,343,758 B2 1/2013 Cheema
8,431,158 B2 4/2013 Shoseyov
8,449,902 B2 5/2013 Brown
8,518,436 B2 8/2013 Voytik-Harbin
8,580,564 B2 11/2013 Brown
8,652,500 B2 2/2014 Bosley, Jr.
8,741,352 B2 6/2014 Hodde
8,785,389 B2 7/2014 Brown
9,101,693 B2 8/2015 Brown
9,205,403 B2 12/2015 Dubois
9,707,703 B2 7/2017 Tully
9,744,123 B2 8/2017 Castiglione-Dodd
9,757,495 B2 9/2017 Murray
10,314,940 B2 6/2019 Voytik-Harbin
11,739,291 B2 8/2023 Voytik-Harbin
12,343,450 B2 7/2025 Voytik-Harbin
12,398,368 B2 8/2025 Voytik-Harbin
2002/0000768 A1 1/2002 Baek
2002/0001701 A1 1/2002 Matsunaga
2002/0001727 A1 1/2002 Robbins
2002/0076816 A1 6/2002 Dai
2002/0170120 A1 11/2002 Eckmayer
2002/0172705 A1 11/2002 Murphy
2003/0001133 A1 1/2003 Antika
2003/0002168 A1 1/2003 Richfield
2003/0059406 A1* 3/2003 Spievack ............ A61L 27/3691 424/551
2003/0113302 A1 6/2003 Revazova
2004/0000063 A1 1/2004 Hallee
2004/0000304 A1 1/2004 LeBrun
2004/0000378 A1 1/2004 Lee
2004/0000780 A1 1/2004 Li
2004/0001376 A1 1/2004 Breitwisch
2004/0006395 A1 1/2004 Badylak
2004/0030404 A1 2/2004 Noll
2004/0037813 A1 2/2004 Simpson
2004/0137616 A1 7/2004 Isseroff
2005/0000141 A1 1/2005 Cauley
2005/0000194 A1 1/2005 Friedmann
2005/0001534 A1 1/2005 Moon
2005/0002020 A1 1/2005 Inoue
2005/0002268 A1 1/2005 Otsuka
2005/0002607 A1 1/2005 Neuhaus
2005/0002665 A1 1/2005 Ito
2005/0014181 A1 1/2005 Galis
2005/0019419 A1 1/2005 Badylak
2005/0142161 A1 6/2005 Freeman
2005/0153442 A1 7/2005 Katz
2005/0202058 A1 9/2005 Hiles
2005/0226856 A1 10/2005 Ahlfors
2005/0260748 A1 11/2005 Chang
2005/0266556 A1 12/2005 Yoder
2006/0000142 A1 1/2006 Cui
2006/0001340 A1 1/2006 Pollmann-Retsch
2006/0001475 A1 1/2006 Price
2006/0001656 A1 1/2006 LaViola
2006/0002355 A1 1/2006 Baek
2006/0002573 A1 1/2006 Dale
2006/0014284 A1 1/2006 Graeve
2006/0134072 A1 6/2006 Pedrozo
2006/0147501 A1 7/2006 Hillas
2006/0165667 A1 7/2006 Laughlin
2006/0235511 A1 10/2006 Osborne
2006/0257377 A1 11/2006 Atala
2007/0000265 A1 1/2007 McEnaney
2007/0000776 A1 1/2007 Karube
2007/0001410 A1 1/2007 Thompson
2007/0001906 A1 1/2007 Pelzer
2007/0002694 A1 1/2007 Taugher
2007/0026518 A1 2/2007 Healy
2007/0077652 A1 4/2007 Peled
2007/0190646 A1 8/2007 Engler
2007/0254005 A1* 11/2007 Pathak .................... A61P 31/00 424/423
2007/0269476 A1 11/2007 Voytik-Harbin
2008/0000259 A1 1/2008 Shewchuk
2008/0000703 A1 1/2008 Shindou
2008/0000958 A1 1/2008 Clarke
2008/0001077 A1 1/2008 Nakasugi
2008/0001819 A1 1/2008 Cohen
2008/0001994 A1 1/2008 Kaneko
2008/0002205 A1 1/2008 Keranen
2008/0002680 A1 1/2008 Skalecki
2008/0095815 A1 4/2008 Mao
2008/0181935 A1 7/2008 Bhatia
2008/0199441 A1 8/2008 Peled
2009/0000698 A1 1/2009 Beresford
2009/0001759 A1 1/2009 Kondo
2009/0002693 A1 1/2009 Engelbart
2009/0002801 A1 1/2009 Nakaho

(56) References Cited

U.S. PATENT DOCUMENTS

2009/0003246 A1 1/2009 Hung
2009/0069893 A1 3/2009 Paukshto
2009/0175922 A1 7/2009 Voytik-Harbin
2009/0269386 A1 10/2009 Zubery
2009/0280180 A1 11/2009 Voytik-Harbin
2010/0001195 A1 1/2010 Konkle
2010/0001434 A1 1/2010 Atkin
2010/0002726 A1 1/2010 Kameyama
2010/0119578 A1 5/2010 To
2010/0143476 A1 6/2010 March
2010/0272697 A1 10/2010 Naji
2010/0291532 A1 11/2010 Ngo
2011/0000277 A1 1/2011 Macmanus
2011/0001829 A1 1/2011 Lai
2011/0182962 A1 7/2011 Mckay
2012/0000943 A1 1/2012 Pere
2012/0001152 A1 1/2012 Kim
2012/0001349 A1 1/2012 Harada
2012/0001414 A1 1/2012 Arning
2012/0001717 A1 1/2012 Park
2012/0001895 A1 1/2012 Lin
2012/0002739 A1 1/2012 Peron
2012/0002975 A1 1/2012 Nakazawa
2012/0027732 A1 2/2012 Voytik-Harbin
2012/0115222 A1 5/2012 Voytik-Harbin
2012/0171768 A1 7/2012 Voytik-Harbin
2012/0189588 A1 7/2012 Nahas
2012/0273993 A1 11/2012 Shoseyov
2014/0000568 A1 1/2014 Nishida
2014/0001934 A1 1/2014 Batur
2014/0056865 A1 2/2014 Samaniego
2014/0193473 A1 7/2014 Yoder
2014/0193477 A1 7/2014 Chaikof et al.
2015/0001053 A1 1/2015 Miyamoto
2015/0105323 A1 4/2015 Novak
2016/0001754 A1 1/2016 Kim
2016/0175482 A1 6/2016 Quirk
2018/0000501 A1 1/2018 Baym
2018/0050130 A1 2/2018 Jiang et al.
2019/0003510 A1 1/2019 Chasse
2020/0246507 A1 8/2020 Voytik-Harbin
2022/0257836 A1 8/2022 Voytik-Harbin

FOREIGN PATENT DOCUMENTS

DE 20115753 U1 1/2002
EP 1264878 12/2002
EP 1270672 A1 1/2003
GB 2366736 3/2002
JP H01247082 10/1989
JP 07074239 B 8/1995
JP H0774239 8/1995
JP 2001511431 8/2001
JP 2011525197 9/2011
JP 2013031730 2/2013
JP 2014198270 10/2014
WO 9215676 9/1992
WO 9300441 1/1993
WO 9403119 2/1994
WO 9423016 10/1994
WO 9717038 5/1997
WO 9806445 2/1998
WO 9852637 11/1998
WO 0015765 3/2000
WO 0047219 A2 8/2000
WO 0062833 10/2000
WO 0110355 2/2001
WO 2001023529 4/2001
WO 2001045765 6/2001
WO 0148153 7/2001
WO 0178754 10/2001
WO 0207646 1/2002
WO 2002102237 1/2002
WO 0220729 3/2002
WO 2003068287 8/2003
WO 2003071991 9/2003
WO 03087337 10/2003
WO 03097694 11/2003
WO 2004028404 A2 4/2004
WO 2004060426 7/2004
WO 2006125025 11/2006
WO 2007028079 3/2007
WO 2012004564 1/2012
WO 2013031861 3/2013
WO 2017044847 A1 3/2017
WO 2019023266 A1 1/2019

OTHER PUBLICATIONS

"Artificial Blood Vessel," English translation of Japanese Patent Application Publication No. 3-12169, 1991, 16 pages.

"Basement Membrane" accessed online at http://en.wikipedia.org/wiki/Basement_membrane#Composition on Jun. 11, 2010.

"Density" form Merriam-Webster online, accessed on Feb. 1, 2011.

"Extracellular Matrix" accessed at http://en.wikipedia.org/wiki/Extracellular matrix on Jun. 11, 2010.

"Oligomer", Wikipedia, (20150925), URL: https://en.wikipedia.org/w/index.php?title=Oligomer&oldid=682674890, (Jun. 22, 2018), XP055528063.

"Stem Cells and the future of Regenerative Medicine" published by National Academy of Sciences, p. 19,2002.

Abou-Neel et al. "Use of multiple unconfined compression for fine control of collagen gel scaffold and mechanical properties," Soft Matter, 2006, 2, 986-92.

Asem, E.K et al. "Basal lamina of Avian Ovarian Follicle: Influence On Morphology of Granulosa Cells In-Vitro," Comparative Biochemistry and Physiology, Part C, 125 (2000), pp. 189-201.

Asem, E.K et al. "Effect of Basal Lamina on Progesterone Production by Chicken Granulosa Cells In Vitro—Influence of Follicular Development," Comparative Biochemistry and Physiology, Part C, 125 (2000) pp. 233-244.

Backer, M.P., et al. "Large Scale Production of Monoclonal Antibodies in Suspension Culture," Biotechnology and Bioengineering, 1988, 32, pp. 993-1000.

Badylak, S.T., et al. "Directed Connective Tissue Remodeling, Upon a Biologic Collagen Substrate," J. Cell Biochem. 1992, Supplement 16F, Abstract No. CE 027, p. 124.

Badylak, S.T., et al. "Endothelial Cell Adherence to Small Intestinal Submucosa: An Acellular Bioscaffold," Biomaterials, 1999, 20, pp. 2257-2263.

Bailey JL et al., "Collagen Oligomers Modulate Physical and Biological Properties of Three-Dimensional Self- Assembled Matrices," Biopolymers, 2010; 95(2): 77-93.

Bell, Brett J. et al., "Cell Density and Extracellular Matrix (ECM) Microstructure Control Mechanical Behavior of Engineered Tissue Constructs", 2005 Summer Bioengineering conference, (Jun. 22-26, 2005).

Bell, et al., "Production of a tissue-like structure by contraction of collagen lattices by human fibroblasts of different proliferative potential in vitro," Mar. 1979, Proc. Natl. Sci. USA, 76(3) pp. 1274-1278.

Bhatia, S.N. et al., "Controlling Cell Interactions by Micropatterning in Co-Cultures: Hepatocytes and 3T3 Fibroblasts," Journal of Biomedical Materials Research, 1997, 34, pp. 189-199.

Billiar, Cellular and Biomolecular Mechanics and Mechanobiology, Arnit Gefen, Ed., p. 210 (2011).

Bioartificial Organs, Richard Skalak and Fred Fox, eds. Tissue Engineering, Chapter V. Transplants and Artificial Organs, pp. 209, 211-39, and 241-2 (Alan R. Liss, Inc. 1988).

Bjornsson, S., "Simultaneous Preparation and Quantitation of Proteoglycans by Precipitation with Alcian Blue", Analytical Biochemistry, vol. 210, 1993, pp. 282-291.

Blay et al., "Epidermal Growth Factor Promotes the Chemotactic Migration of Cultured Rat Intestinal Epithelial Cells," J. Cell Physiology, 1985, 124(1) pp. 107-112.

Block, S., "Peroxygen Compounds," Disinfection, Sterilization and Preservation, 4th Edition 1991, pp. 167-181, Phildelphia, Lea, & Febiger.

(56) References Cited

OTHER PUBLICATIONS

Blum, K.M., et al., "Acellular and high-density, collagen-fibril constructs with suprafibrillar organization," Biomaterials Science, The Royal Society of Chemistry, 2016, 4, 711-23.
Boder G.B. et al. "Long-Term Production of Insulin by Isolated Rabbit Pancreatic Islets in Suspension Culture," J. Cell Biol. 1968, 39(16a).
Boder G.B., et al. "Extended Production of Insulin by Isolated Rabbit Pancreatic Islets; Evidence for Biosynthesis of Insulin," Proc. Soc. Exptl. Biol. Med., 1969, 131, p. 507-513.
Boder, G.B. and Hull, R.H., "Introduction to Techniques in Mammalian Cell Culture," Manual of Industrial Microbiology and Biotechnology, 1983, Ed. A.L. Demain and N.A. Solomon, pp. 248-262.
Boder, G.B., "Mammalian Cell Cultures for Genetically Engineered Products," Toxicologic Pathology, 1989, 17(4) p. 827.
Boder, G.B., et al. "Long Term Monolayer Cultures of Islet Cells from Neonatal Mice," J. Cell Biol., 1973, 59, p. 29a.
Boder, G.B., et al. "Visible Light Inhibits Growth of Chinese Hamster Ovary Cells," European J. Cell Biol., 1983, 31, pp. 132-136.
Boyd et al. Atlas and Text of Corneal Pathology and Surgery; 2011.
Brandner et al., "replicating the Hematopoietic Stem Cell Niche," Purdue University, BME Graduate Student Association Research Symposium, Poster Presentation, Jul. 16, 2009.
Brasack, et al. "Biocompatibility of Modified Silica-Protein Composite Layers," Journal of Sol-Gel Science and Technology, 2000, vol. 19, pp. 479-482.
Brennan and Davison, "Role of aldehydes in collagen fibrillogenesis in vitro," Biopolymers, vol. 19, 1980, Issue 10, p. 1861-1873.
Brightman et al., "Time-Lapse Confocal Reflection Microscopy of Collagen Fibrillogenesis and Extracellular Matrix Assembly In Vitro", Biopolymers, vol. 54, 222-234, (2000).
Brookes, S. et al., "Three-dimensional tissue-engineered skeletal muscle for laryngeal reconstruction: 3D Tissue Engineered Skeletal Muscle," The Laryngoscope, Aug. 26, 2017, 128(3) 603-9.
Brown et al., 2005, Ultrarapid Engineering of Biomimetic Materials and Tissues: Fabrication of Nano- and Microstructures by Plastic Compression, Advanced Functional Materials, 15: 1762-1770. *.
Callister, W. D, Jr., Materials Science and Engineering: an Introduction, 3rd edition, New York, NY, John Wiley & Sons, Inc., 1994.
Campbell, J.H. et al. "Endothelial Cell Influences on Vascular Smooth Muscle Phenotype," Ann. Rev. Physiol., 1986, vol. 48, 384-91.
Case J et al., "Human CD34+AC133+VEGFR-2+ cells are not endothelial progenitor cells but distinct, primitive hematopoietic progenitors," Exp Hematol., 2007; 35(7): 1109-18.
Castano, E., et al., "Inhibition of DNA Synthesis by Aspirin in Swiss 3T3 Fibroblasts," Journal of Pharmacology and Experimental Therapeutics, 1997, 280(1) p. 366-372.
Caves et al., 2011, Elastin-like protein matrix reinforced with collagen microfibers for soft tissue repair, Biomaterials, 32 (23): 5371-5379.
Chandrakasan, Gowri, Dennis A. Torchia, and Karl A. Piez. "Preparation of intact monomeric collagen from rat tail tendon and skin and the structure of the nonhelical ends in solution." Journal of Biological Chemistry 251.19 (1976): 6062-6067.
Chicatun, et al., "Osteoid-Mimicking Dense Collagen/Chitosen Hybrid Gels," BioMacromolecules, 2011, 12, 2946-56.
Chor Wing Tam et al. EWMA Journal, 2012; 12(2).
Ciovacco et al., Bone, 2009, 44(1): 80-86.
Ciovacco, Wendy A., et al. "The role of gap junctions in megakaryocyte-mediated osteoblast proliferation and differentiation." Bone 44.1 (2009): 80-86.
Comper, W. D., and A. Veis, "Characterization of Nuclei in in Vitro Collagen Fibril Formation", Biopolymers, vol. 16, 1977, pp. 2133-2142.
Compston, "Bone marrow and bone: a functional unit," Journal of Endocrinology, 173: 387-394, 2002.
Condell RA et al., "Analysis of Native Collagen Monomers and Oligomers by Size-Exclusion High-Performance Liquid Chromatography and its Application," Analytical Biochemistry, 1993; 212: 436-445.
Critser et al., "Collagen matrix physical properties modulate endothelial colony forming cell-derived vessels in vivo," 2010, Microvasc. Res., 80(1): 23-30.
Davis, et al., "Injectable Self-Assembling Peptide Nanofibers Create Intramyocardial Microenvironments for Endothelial Cells", Circulation, 111, 442-50, (Feb. 1, 2005).
Nguyen et al., "Comparison of the Amino Acid Composition of Two Commercial Porcine Skins (Rind)," Journal of Agricultural and Food Chemistry, 34(3): 565-572 (1986).
Nielsen, T. B. and J. A. Reynolds, "Measurements of Molecular Weights by Gel Electrophoresis", Methods in Enzymology, vol. 48, Hirs and Temasheff, Eds., Academic Press, New York, 1978, pp. 3-10.
Novak et al. "Mechanisms and Microenvironment Investigation of Cellularized High Density Gradient Collagen Matrices via Densification" Adv Funct Mater. Apr. 25, 2016; 26(16): 2617-2628.
Nugent, H.M. et al. "Endothelial Implants inhibit Intimal Hyperplasia After Porcine Angioplasty," Circulation Research, Mar. 5, 1999, 84(4) pp. 384-391.
Office Action for Chinese patent application No. 202180025637.4, dated Jan. 20, 2025. Translation Appended.
Office Action for Japanese Patent Application No. JP2022-545858, dated Dec. 3, 2024. English translation appended.
Office Action for Japanese Patent Application No. JP2022-559920, mailed Apr. 8, 2025 (machine generated translation appended).
Orschell-Traycoff et al., Blood, 2000, 96:1380-1387.
Orschell-Traycoff, Christie M., et al. "Homing and engraftment potential of Sca-1+ lin-cells fractionated on the basis of adhesion molecule expression and position in cell cycle." Blood, The Journal of the American Society of Hematology 96.4 (2000): 1380-1387.
Osborne, et al., "Investigation into the tensile properties of collagen/chondroitin-6-sulphate gels: the effect of crosslinking agents and diamines", Medical & Biological Engineering & Computing, vol. 36, 129-134, (1998).
Ozerdem, et al., "Physical Response of Collagen Gels to Tensile Strain", Journal of Biomechanical Engineering, vol. 117, 397-401, (Nov. 1995).
PCT Search Report and Written Opinion prepared for PCT Application No. PCT/US2021/015277, mailed Apr. 29, 2021.
PCT Search Report and Written Opinion prepared for PCT/US2018/016069, completed Mar. 9, 2018.
Pizzo et al., "Cell-Extracellular Matrix (ECM) Micro-Mechanical Behavior Depends on ECM Microstructure and Cell Type", 2005 Summer Bioengineering Conference, (Jun. 22-26, 2005).
Pizzo et al., "Extracellular matrix (ECM) microstructural composition regulates local cell-ECM biomechanics and fundamental fibroblast behaviour: a multidimensional perspective", JAppl Physiol, 98: 1909-1921, (2005).
Pizzo et al., "Long-term Production of Choline Acetylatransferase in the CNS After Transplantation of Fibroblasts Modified with a Regulatable Vector", Mol Brain Res, 126, 1-13 (2004).
Prater DN et al., "Working hypothesis to redefine endothelial progenitor cells," Leukemia, 2007; 21(6): 1141-9 (Epub Mar. 29, 2007).
Product information: Collagen Solution-Type I from rat tail, Sigma, http://www.siqmaaldrich.com/etc/medialib/docs/Siqma/Datasheet/3/c3867dat.Par.0001.File.tmp/c3867dat.pdf.
Rehman, et al., "Secretion of Angiogenic and Antiapoptotic Factors by Human Adipose Stromal Cells", Circulation, 109: 1292-8, (Mar. 16, 2004).
Reinisch et al., "Humanized large-scale expanded endothelial colony-forming cells function in vitro and in vivo," Blood, 2009; 113:6716-6725.
Reinlib, et al., "Cell Transplantation as Future Therapy for Cardiovascular Disease?", Circulation, 101: e182-e187, (2000).
Roeder B. A., K. Kokini, J. E. Sturgis, J. P. Robinson, S. L. Voytik-Harbin, "Tensile Mechanical Properties of Three-Dimensional Type 1 Collagen Extracellular Matrices with Varied Microstructure", J. Biomech. Eng., vol. 124, 2002, pp. 214-222.

(56) References Cited

OTHER PUBLICATIONS

Roeder et al., "Local, Three-Dimensional Strain Measurements Within Largely Deformed Extracellular Matrix Constructs", J Biomech En , 126, 699-708, (2004.
Rucha Joshi: "Purdue e-Pubs Open Access Dissertations Theses and Dissertations Designer Collagen-Fibril Biograft Materials for Tunable Molecular Delivery," Jan. 1, 2016 https://docs.lib.purdue.edu/open_access_dissertations/1218.
Ruszczak et al., "Effect of collagen matrices on dermal wound healing," Advanced drug Delivery Reviews, 2003, 55, 1595-611.
Sakai et al., Biomaterials 27 (2006) pp. 335-345 (Year: 2006).
Saltzman et al., "Three-dimensional Cell Cultures Mimic Tissues," Ann. N. Y. Acad. Sci., 1992, 665, 259-73.
Sato et al., "Artificial Esophagus," Materials Science Forum, 1997, 250, 105-14.
Scadden, "The stem cell niche as an entity of action," Nature, 441: 1075-1079, 2006.
Schechner et al., "In vivo formation of complex microvessels lined by human endothelial cells in an immunodeficient mouse," PNAS, Aug. 1, 2000, vol. 97, No. 16, 9191-9196.
Schilling, J. A., W. Joel, H. M. Shurley, "Wound Healing: A Comparative Study of the Histochemical Changes in Granulation Tissue Contained in Stainless Steel Wire Mesh and Polyvinyl Sponge Cylinders", Surgery, vol. 46, No. 4, Oct. 1959, pp. 702-710.
Schor et al., "The Use of Three-Dimensional Collagen Gels for the Study of Tumour Cell Invasion In Vitro: Experimental Parameters Influencing Cell Migration Into the Gel Matrix," Int. J. Cancer, 1982, 29, 57-62.
Settleman, "Tension Precedes Commitment—Even for a Stem Cell," Molecular Cell, 2004; 14:148-150.
Shepard et al., 2012, Effect of fiber crosslinking on collagen-fiber reinforced collagen-chondroitin-6-sulfate materials for regenerating load-bearing soft tissues, Journal of Biomedical Materials Research, 101(1): 176-184.
Shields et al., Invasion of Collagen Gels by Mouse Lympoid Cells, Immunology, 1984, 51, 259-68.
Shimizu, "Fabrication of pulsatile cardiac tissue grafts using a novel 3-dimensional cell sheet manipulation technique and temperature-responsive cell culture surfaces," Circ Res., 2002, 90:e40-48.
Shiozawa et al., "The bone marrow niche: habitat to hematopoietic and mesenchymal stem cells, and unwitting host to molecular parasites," Leukemia, 22(5): 941-950, 2008.
Shoulders, et al. "Collagen Structure and Stability," Annu. Rev. Biochem., 2009, 78, 929-58.
Sieminski, A. L., Robert P. Hebbel, and Keith J. Gooch. "The relative magnitudes of endothelial force generation and matrix stiffness modulate capillary morphogenesis in vitro." Experimental cell research 297.2 (2004): 574-584.
Silver et al., "Collagen self-assembly and the development of tendon mechanical properties," Journal of Biomechanics, 2003; 36:1529-1553.
Silver et al., "Type 1 Collagen in Solution," The Journal of Biological Chemistry, 1980, 19(10) 9427-33.
Spradling et al., "Stem Cells Find Their Niche," Nature, 414: 98-104, 2001.
Spradling, Allan, Daniela Drummond-Barbosa, and Toshie Kai. "Stem cells find their niche." Nature 414.6859 (2001): 98-104.
Stem Cell Differentiation (science and global issues/biology, cell biology), 2013.
Stephens, et al., "Oligomeric collagen as an encapsulation material for islet/beta-cell replacement: effect of islet source, dose, implant site, and administration format," Am. J. Physiol. Endocrinol. Metab., 2020, vol. 319, pp. E388-E400.
Strang, et al., Linear Algebra and Its Applications. 3rd edition. San Diego, CA: Academic Press, 1988.
Supplementary European Search Report for EP 18791439.5, completed Dec. 10, 2020.
Sweeney, et al. "Defining the domains of type I collagen involved in heparin-binding and endothelial tube formation," Proceedings of the National Academy of Science, USA 1998, 95, 275-80.
Sykes, B., B. Puddle, M. Francis, and R. Smith, "The Estimation of Two Collagens from Human Dermis by Interrupted Gel Electrophoresis", Biochemical and Biophysical Research Communications, vol. 72, No. 4, 1976, pp. 1472-1480.
Taichman et al., "Human Osteoblasts Support Hematopoiesis through the Production of Granulocyte Colony- stimulating Factor," Journal of Experimental Medicine, 1994; 179:1677-1682.
Junnosuke, "Tissue culture—Basics and Applications-," Asakura Publishing Co., Ltd., 1965, p. 31.
Kacena et al., J. of Histotechnology, 2004, 27:119-130.
Kashtan, H. et al., "Intra-rectal injection of tumor cells: a novel animal model of rectal cancer," Surgical Oncology, 1992, 1,251-6.
Kim, "Characterization of Acid-soluble Collagen from Pacific Whiting Surimi Processing Byproducts," J. Food Science, 2004, 69: C637-C642.
Kleinman, et al., "Membrane Complexes with Biological Activity," Biochemistry, 1986, 25, 312-8.
Kleinman, et al., "Preparation of Collagen Substrates for Cell Attachment: Effect of Collagen Concentration and Phosphate Buffer," Analytical Biochemistry, 1979, 94, 308-12.
Knott et al., "Collagen Cross-Links in Mineralizing Tissues: A Review of Their Chemistry, Function, and Clinical Relevance," 1998, 22(3): 181-187.
Koken, "About Collagen," Technical information, Support webpage, 2006.
Kondo et al., "Biology of Hematopoietic Stem Cells and Progenitors: Implications for Clinical Application," Annu. Rev. Immunol., 2003, 21:759-806.
Kong et al., "FRET measurements of cell-traction forces and nano-scale clustering of adhesion ligands varied by substrate stiffness," PNAS, 2005; 102:4300-4305.
Korff et al., Jour. of Cell Science, vol. 112: 3249-3258 (1999).
Korff, Thomas, and Hellmut G. Augustin. "Tensional forces in fibrillar extracellular matrices control directional capillary sprouting." Journal of cell science 112.19 (1999): 3249-3258.
Kreger et al., "Hyaluronan concentration within a 3D collagen matrix modulates matrix viscoelasticity, but not fibroblast response," Matrix Biol., 2009, 28(6): 336-46.
Kreger et al., "Polymerization and matrix physical properties as important design considerations for soluble collagen formulations," 2010, Biopolymers, 93(8): 690-707.
Kreger, "Design of 3D Collagen Matrices for Cell Delivery and Guidance in Tissue Engineering," Thesis Submitted to the Faculty of Purdue University in Partial Fulfillment of the Requirements for the Degree of Doctor of Philosophy, May 2009, Purdue University.
Kubota, Y. et al., "Role of Laminin and Basement Membrane in the Morphological Differentiation of Human Endothelial Cells into Capillary-like Structures," Journal of Cell Biology, 1988, 107, 1589-98.
Kuo C.Y., et al., "Biohybrid Islet-Gland Equivalent for Transplantation," Journal of Cellular Biochemistry, Supplement 18C PZ110, Feb. 13-26, 1994.
Kuo Ching Chao et al., "A Novel Human Stem Cell Coculture System that Maintains the Survival and Function of Culture Islet-Like Cell Clusters," Cell Transplantation, Jun. 1, 2008, 657-64.
Kuo, C.Y., et al., "Formation of Pseudoislets from Human Pancreatic Cultures," Pancreas, 1992, 7(3) 320-5.
Larsson, L. et al., "Changes in the Islets of Langerhans in the Obese Zucker Rat," Lab. Invest. 1977, 36, 593-8.
Lee et al Journal of Anatomy (2019) 234, pp. 252-262 (Year: 2019).
Lee, et al., "Modulation of Secreted Proteins of Mouse Mammary Epithelial Cells by the Collagenous Substrata," The Journal of Cell Biology, 1984, 98, 146-55.
Lillie et al., "Growth of Stratified Squamous Epithelium on Reconstituted Extracellular Matrices: Long-Term Culture," Journal of Investigative Dermatology, 1988, 90(2) 100-9.
Lin et al., "Comparison of Physical-Chemistry Properties of Type I Collagen from Different Species," Food Chemistry, 99(2): 244-251 (2005).
Liu, Asian-Aust J. Anim. Sci, 2001; 14(11): 1638-1644.
Liu, C. H., et al., "Effects of Salvianolic Acid-A on NIH/3T3 Fibroblast Proliferation, Collagen Synthesis and Gene Expression," World J. Gastroentero, 2000, 6(3) 361-4.

(56) References Cited

OTHER PUBLICATIONS

Liu, D. C., Y. K. Lin, and M. T. Chen. "Optimum condition of extracting collagen from chicken feet and its charecetristics." Asian-Australasian journal of animal sciences 14.11 (2001): 1638-1644.
Lynn et al., "Antigenicity and immunogenicity of collagen," . 1 Biomed Mater Res, Part B: Appl Biomater, 2004; 71B: 343-354.
Malvern, Introduction to the Mechanics of a Continuous Medium. Upper Saddle River, NJ: Prentice-Hall, 1969.
Marotta, M., G. Martino, "Sensitive Spectrophotometric Method for the Quantitative Estimation of Collagen", Analytical Biochemistry, vol. 150, 1985, pp. 86-90.
Maru et al., "An Oncogenic Form of the Fit-1 Kinase has a Tubulogenic Potential in a Sinusoidal Endothelial Cell Line," European Journal of Cell Biology, 2000, 79, 130-43.
McBeath et al., "Cell shape, cytoskeletal tension, and RhoA regulate stem cell lineage commitment," Developmental Cell, 2004; 6:483-495.
Merriam-Webster, Engineer definition, retrieved from the internet Jan. 27, 2022: https://www.merriam-webster.com/dictionary/engineer (Year: 2022).
Merriam-Webster: definition of "synthesis", retrieved from the internet, Sep. 1, 2022: https://www.merriam-webster.com/dictionary/synthetic (Year: 2022).
Michalopoulos & Pitot, "Primary Culture of Parenchymal Liver Cells on Collagen Membranes," Experimental Cell Research, 1975, 94, 70-8.
Mienaltowski et al., 2014, Structure, Physiology, and Biochemistry of Collagens, Advances in Experimental Medicine and Biology, 802: 5-29. *.
Mikos, A.G., et al., "Islet Transplantation to Create a Bioartificial Pancreas," Biotech. and Bioengineering, 1994, 43, 673-7.
Miller et al., "Preparation and Characterization of the Different Types of Collagen," Methods in Enzymology, 82: 33-64 (1982).
Miller, E. J., E. H. Epstein, Jr., and K. A. Piez, "Identification of three Genetically Distinct Collagens by Cyanogen Bromide Cleavage of Insoluble Human Skin and Cartilage Collagen", Biochemical and Biophysical Research Communications, vol. 42, No. 6, 1971, pp. 1024-1029.
Mitra et al., 2012, Preparation and characterization of malonic acid cross-linked chitosan and collagen 3D scaffolds: an approach on non-covalent interactions, J Mater Sci: Mater Med, 23: 1309-1321.
Mizuno et al., "Osteogenesis by bone marrow stromal cells maintained on type 1 collagen matrix gels in vivo." Bone 20:101-107 (1997).
Mokonjimobe et al., "Hexosaminidase and alkaline phosphatase activities in articular chondrocytes and relationship to cell culture conditions," Experientia, 1992, 48(4) 396-8.
Munakata, et al., Glycobiology, vol. 9, 1023-1027 (1999).
Munakata, Hidekazu, et al. "Interaction between collagens and glycosaminoglycans investigated using a surface plasmon resonance biosensor." Glycobiology 9.10 (1999): 1023-1027.
Mund JA et al., "Endothelial progenitor cells and cardiovascular cell-based therapies," Cytotherapy, 2009: 11(2): 103-13.
Na et al., "In Vitro Collagen Fibril Assembly in Glycerol Solution: Evidence for a Helical Cooperative Mechanism Involving Microfibrils," Biochemistry, 1986; 25: 958-966.
Na et al., "Mechanism of in Vitro Collagen Fibril Assembly," Journal of Biological Chemistry, 1986; 261(26): 12290-12299.
Na, "Monomer and Oligomer of Type I Collagen: Molecular Properties and Fibril Assembly," Biochemistry, 1989, 28 (18):7161-7167.
Narmoneva et al., "Endothelial Cells Promote Cardiac Myocyte Survival and Spatial Reorganization", Circulation, 110, 962-968, (Aug. 24, 2004).
Nerem, R., "Tissue Engineering: The Hope, The Hype and The Future," Tissue Engineering, 2006, 12(5) 1143-50.
Takahashi, et al., "Compressive force promotes Sox9, type II collagen and aggrecan and inhibits IL-1B expression resulting in chondrogenesis in mouse embryonic limb bud mesenchymal cells." Journal of Cell Science, 1998, 111(14) 2067-76.
Taqvi et al., "Influence of scaffold physical properties and stromal cell coculture on hematopoietic differentiation of mouse embryonic stem cells," Biomaterials, 2006; 24:6024-6031.
Tebmar et al., "Hydrogels for tissue engineering," Fundamentals of Tissue Engineering and Regenerative Medicine, 2009; p. 495-517.
Timmermans F et al., "Endothelial progenitor cells: identify defined?", J Cell Mol Med, 2009; 13(1): 87-102.
Vasiliev and Gelfand, Neoplastic and Normal Cells in Culture, Cambring University Press, p. 19, 1981.
Veis, Arthur, et al., "Fundamentals of Interstitial; Collagen Self-Assembly", 1994, Extracellular Matrix Assembly and Structure, Academic Press, pp. 15-45.
Vescoi et al., "In vivo-like drug responses of human tumors growing in three-dimensional gel-supported primary culture," Proc. Natl. Acad. Sci. USA, 1987, 84, 5029-33.
Volpi et al., 1991, On the adaptive structures of the collagen fibrils of bone and cartilage, J Biomech, 24(Suppl 1): 67-77 (abstract only). *.
Voytik-Harbin et al., "Application and Evaluation of the Alamarblue Assay For Cell Growth and Survival of Fibroblasts", In Vitro Cell Dev Biol Anim, 34, 239-246, (1998).
Voytik-Harbin et al., "Identification of Extractable Growth Factors from Small Intestine Submucosa," J Cell. Biochemistry, 1997; 67: 478-491.
Voytik-Harbin et al., "Simultaneous Mechanical Loading and Confocal Reflection Microscopy for Three-Dimensional Microbiomechanical Analysis of Biomaterials and Tissue Constructs", Microsc Microanal, 9, 74-85, (2003).
Voytik-Harbin et al., Small Intestinal Submucosa: A Tissue-Derived Extracellular Matrix That Promotes Tissue-Specific Growth and Differentiation of Cells in Vitro, Tissue Engineering, 4, 2, 157-174, (1998).
Voytik-Harbin et al., "Three-Dimensional Imaging of Extracellular Matrix and Extracellular Matrix-Cell Interactions", Methods In Cell Biology, 63, 583-597, (2001).
Wakitani et al., "Mesenchymal Cell-Based Repair of Large, Full Thickness Defects of Articular Cartilage," J. Bone Joint Surg. Am., Abstract, 1994, 76(4) 579-92.
Wang et al., Sheng Li Xue Bao, 2005, 57(2): 259-269; Abstract Only.
Wess, Collagen fibrillar structure and hierarchies in P. Fratzl (ed.), Collagen: Structure and Mechanics, Springer Science + Business Media, LLC, New York, 2008, 53-60.
Whittington et al., "Collagen oligomers modulate physical and cell-instructive properties of polymerizable collagen matrices," Biomaterials Day Society for Biomaterials, Nov. 6, 2010 (PowerPoint presentation and poster).
Whittington, C, et al., "Oligomers Modulate Interfibril Branching and Mass Transport Properties of Collagen Matrices," Microsc Microanal, Oct. 2013, 19(5) 20 pages.
Whittington, C.F., et al., "Collagen-Polymer Guidance of Vessel Network Formation and Stabilization by Endothelial Colony Forming Cells In Vitro," Macromolecular Bioscience, 2013, 13, 1135-49.
Whittington, Catherine F., et al. "Oligomers modulate interfibril branching and mass transport properties of collagen matrices." Microscopy and Microanalysis 19.5 (2013): 1323-1333. (Year: 2013).
Williams et al., 1978, Journ Biol Chem, 253: 6578-6585.
Wilson, et al. "A fibril-reinforced poroviscoelastic swelling model for articular cartilage," Journal of biomechanics, 2005, 38(6) pp. 1195-1204.
Wu et al.: "Bioprinting three-dimensional cell-laden tissue constructs with controllable degradation", Scientific Reports, vol. 6, No. 1, Apr. 19, 2016, pp. 1-10, XP055528074.
Xi, et al. "Pore size and pore-size distribution control of porous silica," Sensors and Actuators, 1995, vol. B 24-25, pp. 347-352.
Yang, E.K. et al., "Tissue Engineered Artificial Skin Composed of Dermis and Epidermis," International Society for Artificial Organs, 2000, 24(1) 7-17.
Yang, et al., "The application of recombinant human collagen in tiussue engineering." Biodrugs 18:103-119 (2004).

(56) References Cited

OTHER PUBLICATIONS

Yoder et al., "Redefining endothelial progenitor cells via clonal analysis and hematopoietic stem/progenitor cell principals," BLOOD, 2007, 109:1801-1809.
Young et al., "Use of meschymal stem cells in a collagen matrix for Achilles tendon repair.—J. Ortopaedic Res. 16"406-413 (1998).
Young, et al., "Adult Stem Cells." Anat. Record Pt. A: Disc. Mol. Cell. Evol. Biol. 276A:75-102 (2004).
Zhu et al., 2014, Designed composites for mimicking compressive mechanical properties of articular cartilage matrix, Journal of the Mechanical Behavior of Biomedical Materials, 36: 32-46. *.
Zitnay et al., "Fabrication of dense anisotropic collagen scaffolds using biaxial compression," Acta Biomaterialia, vol. 65, 2018, pp. 76-87, DOI: 10.1016/j.actbio.2017.11.017.
Zorlutuna et al., "Nanopatterning of Collagen Scaffolds Improve the Mechanical Properties of Tissue Engineered Vascular Graft," Biomacromolecules, 2009, 10, 814-21.
Delcourt-Huard, et al., "Reconstituted Human Gingivial Epithelium: Nonsubmerged In Vitro Model," In Vitro Cellular & Developmental Biology Animal, Jan. 1997, 33(1) p. 30-36.
Deluca, et al., "Evidence That Human Oral Epithelium Reconstituted In Vitro and Transplanted on Patients with Defects in the Oral Mucosa Retains Properties of the Original Donor Site," Transplantation, 1990, 50(3) p. 454-459.
Denton, G.W., "Chlorhexidine," Disinfection, Sterilization and Preservation, 4th Edition 1991, Philadelphia, Lea, & Febiger, p. 274-289.
Elsdale and Bard, "Collagen Substrata for Studies on Cell Behavior," The Journal of Cell Biology, 1972, 54, p. 626-637.
Emerman et al., "Maintenance and Induction of Morphological Differentiation in Dissociated Mammary Epithelium on floating Collagen Membranes," In Vitro, 1977, 13(5) pp. 316-328.
Engler et al., "Matrix elasticity directs stem cell lineage specification," Cell, 2006; 126:677-689.
Engler et al., "Myotubes differentiate optimally on substrates with tissue-like stiffness: pathological implications for soft or stiff microenvironments," Journal of Cell Biology, 2004; 165:877-887.
Engler et al., "Substrate elasticity directs adult mesenchymal stem cell differentiation," Abstract 783, The 37th Middle Atlantic Regional Meeting, May 2005.
Extended European Search Report for EP patent application No. 21747781.9, dated Jan. 23, 2024.
Fischbach, et al., "Three-dimensional in vitro model of adipogenesis: coparison of culture conditions." Tissue Engineering 10:215-229 (2004).
Fogolia, et al. "A new method for the preparation of biocompatible silica coated-collagen hydrogels," J. Mater. Chem. B., 2013, vol. 1, pp. 1283-1290.
Francis, et al. "Endothelial cell-matrix interactions in neovascularization," Tissue Engineering Part B: Reviews, 2008, 14(1) 19-32.
Freed et al., "Joint Resurfacing Using Allograft Chondrocytes and Synthetic Biodegradable Polymer Scaffolds," J. Biomedical Materials Res., 1994, 28, p. 891-899.
Freeman et al., "In vivo-like growth of human tumors in vitro," Proc. Natl. Acad. Sci. USA, Apr. 1986, 83, 2694-8.
Freshney, R.I., "Culture of Animal Ceils: A Manual of Basic Technique," Chapters 12 and 13, Alan R. Liss. Inc., New York (1994) p. 119-143.
Friess, "Collagen-biomaterial for drug delivery," European Journal of Pharmaceutics and Biopharmaceutics, 1998, 45 (2) 113-36.
Fulzele, S. V., P. M. Satturwar, A. K. Doyle, "Study of the Biodegradation and in Vivo Biocompatibility of Novel Biomaterials", European Journal of Pharmaceutical Sciences, vol. 20, 2003, pp. 53-61.
Gallagher D, "Stem cells being made from blood," available at www.bbc.co.uk/news/health-20539835.
Gallop, P. M., and S. Seifter, "Preparation and Properties of Soluble Collagens", Soluble Collagens, 1963, pp. 635-641.
Gelman et al., "Collagen Fibril Formation in Vitro," J. Biol. Chem., 1979, 254(22): 11741-11745.
Gelman et al., "Collagen Fibril Formation," J. Biol. Chem., 1979, 254(1): 180-186.
Girasole et al., "17-B Estradiol Inhibits IL-6 Production by Bone Marrow-Derived Stromal Cells and osteoblasts In Vitro: A Potential Mechanism for the Antiosteoporotic Effects of Estrogens," The Journal of Clinical Investigation, Inc. 1992, 89,-883-91.
Glowacki, J. and Mizuno, S. "Collagen Scaffolds for Tissue Engineering," Biopolymers, 2007, 89, 338-44.
Griffey, S., N. D. Schwade, C. G. Wright, "Particulate Dermal Matrix as an Injectable Soft Tissue Replacement Material", J. Biomed. Mater. Res. vol. 58, 2001, pp. 10-15.
Grinnel, "Cell-Collagen Interactions: Overview," Methods in Enzymology, 1982, 82, 499-503.
Grover et al., 2012, Crosslinking and composition influence the surface properties, mechanical stiffness and cell reactivity of collagen-based films, Acta Biomater, 8(8): 3080-3090.
Hambli et al., "Physically based 3D finite element model of a single mineralized collagen microfibril," Journal of Theoretical Biology, 2012, 301, 28-41.
Hayashi, "The effect of three-dimensional structure of extracellular matrix on cellular functions including response to growth factors," Biophysics, 1992, 32(4) p. 211-215.
Hirschi KK et al., "Assessing identify, phenotype, and fate of endothelial progenitor cells," Arterioscler Thromb Vasc Biol, 2008; 28(9): 1584-95 (Epub Jul. 31, 2008).
Hirschi, K.K et al. "PDGF, TGF-β, and Heterotypic Cell-Cell Interactions Mediate Endothelial Cell-Induced Recruitment of 10T1/2 Cells and Their Differentiation to a Smooth Muscle Fate," The Journal of Cell Biology, 1998, 141(3) pp. 805-814.
Ho et al., "Characterization of Collagen Isolation and Application of Collagen Gel as a Drug Carrier", J. of Controlled Release, vol. 44, pp. 103-112 (1997).
Ho, M., et al., "Identification of Endothelial Cell Genes by Combined Database Mining and Microarray Analysis," Physiol. Genomics, 2003, 13, 249-62.
Hou, et al., "Radiolabeled Cell Distribution After Intramyocardial, Intracoronary, and Interstitial Retrograde Coronary Venous Delivery", Circulation, 112, 150-6, (Aug. 30, 2005).
Huang et al., 2005, Mechanisms and Dynamics of Mechanical Strengthening in Ligament-Equivalent Fibroblast-Populated Collagen Matrices, Annals of Biomedical Engineering, 21: 289-305.
Hunt, T. K., P. Twomey, B. Zederfeldt, and J. E. Dunphy, "Respiratory Gas Tensions and PH In Healing Wounds", American Journal of Surgery, vol. 114, 1967, pp. 302-307.
Ibrahiem, E.I.H., et al. "Orthotopic Implantation of Primary N-[4-(5-Nitro-2-furyl)-2-thiazolyl]formamide-induced Bladder Cancer in Bladder Submucosa: An Animal Model for Bladder Cancer Study," Cancer Research, 1983, 43, 617-20.
Ingram D et al., "Unresolved questions, changing definitions, and novel paradigms for defining endothelial progenitor cells via clonal analysis and hematopoietic stem/progenitor cell principals," Blood, 2007; 109(5): 1801-9 (Epub Oct. 19, 2006).
Ingram D et al., "Vessel wall-derived endothelial cells rapidly proliferate because they contain a complete hierarchy of endothelial progenitor cells," Blood, 2005; 105(7):2783-6 (Epub Dec. 7, 2004).
Ingram, D. A., et al., "Identification of a Novel Hierarchy of Endothelial Progenitor Cells Using Human Peripheral and Umbilical Cord Blood", Blood, 104, 2752-2760, (2004).
International Preliminary Report on Patentability and Written Report for PCT/US2006/018998; 9 pages.
International Preliminary Report on Patentability and Written Report for PCT/US2006/019130; 8 pages.
International Search Report and Written Opinion for PCT/US2008/086232, Jan. 16, 2009, 12 pages.
International Search Report and Written Opinion for PCT/US2010/042290; 13 pages.
International Search Report and Written Opinion for PCT/US2012/040737; 6 pages.
International Search Report and Written Opinion for PCT/US2015/047176; 12 pages.
International Search Report and Written Opinion issued by the ISA/US Commissioner for Patents, dated Jul. 6, 2018, for International Application No. PCT/US2018/029473.

(56) References Cited

OTHER PUBLICATIONS

International Search Report for International Application No. PCT/US07/020463, Feb. 21, 2008, 6 pgs.
International Search Report/Written Opinion for PCT/US2007/011681 completed Nov. 6, 2007.
Ji et al., 2012, Mechanics of electrospun collagen and hydroxyapatite/collagen nanofibers, Journal of the Mechanical Behavior of Biomedical Materials, 13: 185-193.
JPK Instruments, Collagen: levels of structure and alignment, pp. 1-6, retrieved from the internet Jan. 27, 2022: https://www.jpk.com/app-technotes-img/AFM/pdf/jpk-app-collagen.14-1.pdf (Year: 2022).

* cited by examiner

PC GTA

HIGH-STRENGTH COLLAGEN COMPOSITIONS AND METHODS OF USE

CROSS-REFERENCE TO RELATED APPLICATIONS

This application is a national stage entry under 35 USC § 371(b) of PCT International Application No. PCT/US2021/024893, filed Mar. 30, 2021, which claims priority under 35 U.S.C. § 119 (e) to U.S. Provisional Application Ser. No. 63/002,644 filed on Mar. 31, 2020, the entire disclosures of which are incorporated herein by reference.

TECHNICAL FIELD

The invention relates to engineered collagen scaffolds with a thickness from about 0.005 mm to about 3 mm, and with a high strength (e.g., a high elastic modulus of from about 0.5 MPa to about 200 MPa). The engineered collagen scaffolds can be non-collapsible and/or non-expandable. This disclosure also relates to methods of use of these collagen scaffolds.

BACKGROUND AND SUMMARY

The ability to replace, restore, or regenerate damaged or dysfunctional tissues in patients represents a great challenge in medicine. An important component of all tissues and organs, is the extracellular matrix (ECM), which represents the non-living material within which living cells are distributed and organized. The ECM provides the physical scaffolding that not only determines the mechanical properties of tissues but also supports cells in three dimensions. In addition, the ECM serves as a critical regulator of cell behavior, informing cells through essential biochemical and biomechanical signaling. Given the importance of the ECM to overall tissue structure and function, tissue engineering and regenerative medicine efforts have focused on the development of materials that recreate ECM scaffolds for improved tissue reparation, restoration, and regeneration outcomes.

Collagen is the most abundant protein of the ECM and body, where it serves as the major determinant of the structural and mechanical properties of tissues. Within the body, collagen is produced by cells as a single molecule, consisting of a three polypeptide chains. Individual collagen molecules, also known as tropocollagen, have a central triple helical domain capped at both ends by more randomly organized telopeptides. Since in vivo individual collagen molecules (monomers) undergo hierarchical self-assembly to form polymeric materials (e.g., insoluble fibrillar matrices of the ECM), collagen is not only a protein but also a polymer. During in-vivo synthesis and assembly, these polymeric collagen materials are further stabilized by the formation of natural intra- and inter-molecular crosslinks, which serve to impart mechanical strength and control collagen turnover (i.e., the balance between collagen degradation and synthesis). Because of its dual role as a structural and cellular signaling element of the ECM, collagen has been a preferred biomaterial in both research and clinical settings. Its high availability in the body, conservation across tissues and species, predictive degradability into by-products by proteolytic enzymes (e.g., matrix metalloproteinases), and high biocompatibility also make it ideally suited for tissue engineering and regenerative medicine applications.

To date, engineered collagen scaffolds known in the art have typically been fashioned from collagen monomers known as telocollagen and atelocollagen. Telocollagen represents the full length tropocollagen molecule, which is commonly isolated from tissues via acid extraction. Atelocollagen, represents a modified version of the natural tropocollagen molecule, where the telopeptide ends have been enzymatically cleaved during the protein isolation and purification process. The shortcomings of these collagen monomers for preparation of collagen materials are well established and include significant lot-to-lot variability in purity and polymerization capacity, long polymerization times (often greater than 30 minutes), poor stability and mechanical integrity of formed polymeric materials, and rapid proteolytic degradation of formed polymeric materials in vitro and in vivo. The instability of collagen materials formed from telocollagen and atelocollagen has led to a need for additional material processing strategies to improve material stiffness (elastic modulus) and strength and resistance to proteolytic degradation. These material processing strategies primarily use exogenous crosslinking via physical and chemical means or copolymerization with other materials. While such strategies have had varying success at improving the mechanical properties and stability of collagen materials, they are known to have deleterious effects on the inherent biological signaling capacity of collagen, resulting in adverse tissue responses, including inflammatory and foreign body reactions. Furthermore, the achievable density of materials prepared from telocollagen and atelocollagen has been limited and is much less than the collagen density (concentration) found in connective tissues in vivo. This observation is of vital importance because the physical features of collagen materials, including scaffold stiffness and collagen density, has been shown to directly impact fundamental cellular behaviors, including proliferation, migration, and differentiation processes that occur during tissue repair and regeneration.

Accordingly, there exists a need for high-strength collagen scaffolds that are made without using deleterious exogenous processing or cross-linking strategies, and that approach the in vivo structure and functionality of natural collagen scaffolds to provide advantages in the fields of tissue engineering and regenerative medicine. Surprisingly, the inventors have developed engineered collagen scaffolds with a thickness of about 0.005 mm to about 3 mm, and with a high strength (e.g., a high elastic modulus of about 0.5 MPa to about 200 MPa). In one aspect, these collagen scaffolds can be non-collapsible and/or non-expandable, and are similar in strength to high-strength tissues found in vivo such as pericardium, amniotic membrane, heart valves, and the like. Additionally, high-strength properties facilitate material manipulation and application when used clinically for tissue replacement and reconstruction procedures.

The engineered collagen scaffolds of the present disclosure provide several advantages compared to those known in the art. First, the engineered collagen scaffolds of the present disclosure possess improved mechanical properties compared to those in the art. In particular, the engineered collagen scaffolds of the present disclosure are not fragile and have improved mechanical properties (e.g., a high elastic modulus of from about 0.5 MPa to about 200 MPa) without employing exogenous cross-linking and processing strategies known to be deleterious to natural collagen biosignaling and the in vivo tissue response. Furthermore, the engineered collagen scaffolds of the present disclosure have improved resistance to degradation, slow turnover, and the engineered collagen scaffolds of the present disclosure do not induce inflammatory or foreign body reactions.

In one embodiment, a non-collapsible and/or non-expandable engineered collagen scaffold is provided. The collagen scaffold has a thickness of from about 0.005 mm to about 3 mm and an elastic modulus of from about 0.5 MPa to about 200 MPa.

In another embodiment, a method of treating a patient to regenerate, restore, or replace a damaged or a dysfunctional tissue is provided. The method comprises implanting into the patient a medical graft comprising any of the engineered collagen scaffolds described herein.

Additional embodiments are also described by the following enumerated clauses. Any of the following embodiments in combination with any applicable embodiments described in the Background and Summary section, the Detailed Description of the Illustrative Embodiments section, the Examples section, or the claims of this patent application, are also contemplated.

1. A non-collapsible and/or non-expandable engineered collagen scaffold, wherein the collagen scaffold has a thickness of from about 0.005 mm to about 3 mm and an elastic modulus of from about 0.5 MPa to about 200 MPa.
2. The engineered collagen scaffold of clause 1, wherein the collagen scaffold does not collapse when the collagen scaffold is lyophilized and rehydrated.
3. The engineered collagen scaffold of any one of clauses 1 to 2, wherein the collagen scaffold has a thickness of from about 0.01 mm to about 2.0 mm.
4. The engineered collagen scaffold of any one of clauses 1 to 2, wherein the collagen scaffold has a thickness of from about 0.01 mm to about 1.0 mm.
5. The engineered collagen scaffold of any one of clauses 1 to 2, wherein the collagen scaffold has a thickness of from about 0.01 mm to about 0.25 mm.
6. The engineered collagen scaffold of any one of clauses 1 to 2, wherein the collagen scaffold has a thickness of from about 0.1 mm to about 1.0 mm.
7. The engineered collagen scaffold of any one of clauses 1 to 2, wherein the collagen scaffold has a thickness of from about 0.5 mm to about 1.0 mm.
8. The engineered collagen scaffold of any one of clauses 1 to 2, wherein the collagen scaffold has a thickness of from about 0.15 mm to about 0.25 mm.
9. The engineered collagen scaffold of any one of clauses 1 to 8, wherein the collagen scaffold has an elastic modulus of from about 18 MPa to about 200 MPa.
10. The engineered collagen scaffold of any one of clauses 1 to 8, wherein the collagen scaffold has an elastic modulus of from about 20 MPa to about 180 MPa.
11. The engineered collagen scaffold of any one of clauses 1 to 8, wherein the collagen scaffold has an elastic modulus of from about 40 MPa to about 120 MPa.
12. The engineered collagen scaffold of any one of clauses 1 to 8, wherein the collagen scaffold has an elastic modulus of from about 60 MPa to about 100 MPa.
13. The engineered collagen scaffold of any one of clauses 1 to 8, wherein the collagen scaffold has an elastic modulus of from about 80 MPa to about 180 MPa.
14. The engineered collagen scaffold of any one of clauses 1 to 8, wherein the collagen scaffold has an ultimate tensile strength of from about 0.5 MPa to about 20 MPa.
15. The engineered collagen scaffold of any one of clauses 1 to 8, wherein the collagen scaffold has an ultimate tensile strength of from about 1 MPa to about 25 MPa.
16. The engineered collagen scaffold of any one of clauses 1 to 15, wherein the collagen scaffold has an ultimate tensile strength of from about 0.2 MPa to about 20 MPa.
17. The engineered collagen scaffold of any one of clauses 1 to 15, wherein the collagen scaffold has an ultimate tensile strength of from about 5 MPa to about 15 MPa.
18. The engineered collagen scaffold of any one of clauses 1 to 15, wherein the collagen scaffold has an ultimate tensile strength of from about 2 MPa to about 20 MPa.
19. The engineered collagen scaffold of any one of clauses 1 to 18, wherein the collagen scaffold has a failure strain of from about 5% to about 70%.
20. The engineered collagen scaffold of any one of clauses 1 to 18, wherein the collagen scaffold has a failure strain of from about 10% to about 40%.
21. The engineered collagen scaffold of any one of clauses 1 to 20, wherein the collagen scaffold has a suture retention peak load of from about 2 N to about 8 N.
22. The engineered collagen scaffold of any one of clauses 1 to 20, wherein the collagen scaffold has a suture retention peak load of from about 0.2 N to about 2 N.
23. The engineered collagen scaffold of any one of clauses 1 to 20, wherein the collagen scaffold has a suture retention peak load of from about 0.1 N to about 4 N.
24. The engineered collagen scaffold of any one of clauses 1 to 23, wherein the engineered collagen scaffold is in a composition and the composition further comprises fluid.
25. The engineered collagen scaffold of clause 24, wherein the percentage of fluid present is from about 5% to about 99%.
26. The engineered collagen scaffold of any one of clauses 24 or 25, wherein the composition is dried by lyophilizing the composition, vacuum pressing the composition, or by dehydrothermal treatment, or a combination thereof.
27. The engineered collagen scaffold of any one of clauses 1 to 26, wherein the collagen is Type I collagen.
28. The engineered collagen scaffold of any one of clauses 1 to 27, wherein the collagen is purified Type I collagen.
29. The engineered collagen scaffold of any one of clauses 1 to 28, wherein the engineered collagen scaffold is a medical graft.
30. The engineered collagen scaffold of any one of clauses 1 to 29, wherein the engineered collagen scaffold is a medical graft and the medical graft is used for the regeneration, the restoration, or the replacement of a damaged or a dysfunctional tissue.
31. The engineered collagen scaffold of clause 30, wherein the engineered collagen scaffold is a medical graft for regeneration or replacement or restoration of a tissue selected from pericardium, heart valve, skin, blood vessels, airway tissue, body wall, and tissue reconstructed following tumor removal.
32. The engineered collagen scaffold of any one of clauses 1 to 31, wherein the engineered collagen scaffold is terminally sterilized or prepared aseptically.
33. The engineered collagen scaffold of clause 32 wherein the collagen scaffold is terminally sterilized by a process selected from treatment with glutaraldehyde, gamma irradiation, electron beam irradiation, or ethylene oxide treatment.
34. The engineered collagen scaffold of any one of clauses 1 to 33, wherein the collagen comprises oligomeric collagen, monomeric collagen, telocollagen, or atelocollagen, or a combination thereof.

35. The engineered collagen scaffold of any one of clauses 1 to 34 compressed into a defined shape.

36. The engineered collagen scaffold of clause 35, wherein the shape is a sphere.

37. The engineered collagen scaffold of clause 35, wherein the shape is a tube.

38. The engineered collagen scaffold of clause 35, wherein the shape is a sheet.

39. The engineered collagen scaffold of any one of clauses 35 to 38, wherein the compression is confined compression.

40. The engineered collagen scaffold of any one of clauses 1 to 39, wherein the collagen concentration is from about 50 to about 1000 mg/cm$^3$.

41. The engineered collagen scaffold of any one of clauses 1 to 39, wherein the collagen concentration is from about 50 to about 900 mg/cm$^3$.

42. The engineered collagen scaffold of any one of clauses 1 to 39, wherein the collagen concentration is from about 50 to about 800 mg/cm$^3$.

43. The engineered collagen scaffold of any one of clauses 1 to 39, wherein the collagen concentration is from about 50 to about 700 mg/cm$^3$.

44. The engineered collagen scaffold of any one of clauses 1 to 39, wherein the collagen concentration is from about 50 to about 600 mg/cm$^3$.

45. The engineered collagen scaffold of any one of clauses 1 to 39, wherein the collagen concentration is from about 50 to about 500 mg/cm$^3$.

46. The engineered collagen scaffold of any one of clauses 1 to 39, wherein the collagen concentration is from about 50 to about 400 mg/cm$^3$.

47. The engineered collagen scaffold of any one of clauses 1 to 39, wherein the collagen concentration is from about 50 to about 300 mg/cm$^3$.

48. The engineered collagen scaffold of any one of clauses 1 to 39, wherein the collagen concentration is from about 50 to about 200 mg/cm$^3$.

49. The engineered collagen scaffold of any one of clauses 1 to 48, wherein the engineered collagen scaffold does not induce an inflammatory or a foreign body reaction when implanted into a patient.

50. The engineered collagen scaffold of any one of clauses 1 to 49 wherein the collagen is selected from pig collagen, human collagen, and bovine collagen.

51. The engineered collagen scaffold of any one of clauses 1 to 49, wherein the collagen is synthetic collagen.

52. The engineered collagen scaffold of any one of clauses 1 to 50, wherein the collagen is native collagen.

53. The engineered collagen scaffold of any one of clauses 1 to 49, wherein the collagen is recombinant collagen.

54. The engineered collagen scaffold of any one of clauses 1 to 53 further comprising cells.

55. The engineered collagen scaffold of clause 54, wherein the cells are stem cells.

56. A method of treating a patient to regenerate, restore, or replace a damaged or a dysfunctional tissue, the method comprising implanting into the patient a medical graft comprising the engineered collagen scaffold of any one of clauses 1 to 55.

57. The method of clause 56, wherein the medical graft is for the regeneration, restoration, or replacement of damaged or dysfunctional pericardium.

58. The method of clause 56, wherein the medical graft is for the regeneration, restoration, or replacement of damaged or dysfunctional heart valve.

59. The method of clause 56, wherein the medical graft is for the regeneration, restoration, or replacement of damaged or dysfunctional skin.

60. The method of clause 59, wherein the valve tissue is aortic valve tissue or pulmonic valve tissue.

61. The engineered collagen scaffold of any one of clauses 1 to 55 or the method of any one of clauses 56 to 60 wherein the engineered collagen scaffold is exogenously cross-linked.

62. The engineered collagen scaffold or the method of clause 61 wherein the engineered collagen scaffold is cross-linked with glutaraldehyde.

BRIEF DESCRIPTION OF THE DRAWINGS

FIG. 3, right panel shows a photograph of a representative prototype collagen scaffold (6.3 cm diameter) prepared by compression dehydration using Formula 4.

FIG. 8, top panel, shows the results for an uncompressed sample (14 mm thick) prepared from 3.5 mg/ml oligomer collagen and FIG. 8, lower panel, shows the results for a resultant collagen sheet (2 mm thick and approximately 24.5 mg/ml) following compression at 6 mm/min.

DETAILED DESCRIPTION OF THE ILLUSTRATIVE EMBODIMENTS

Figure 1:
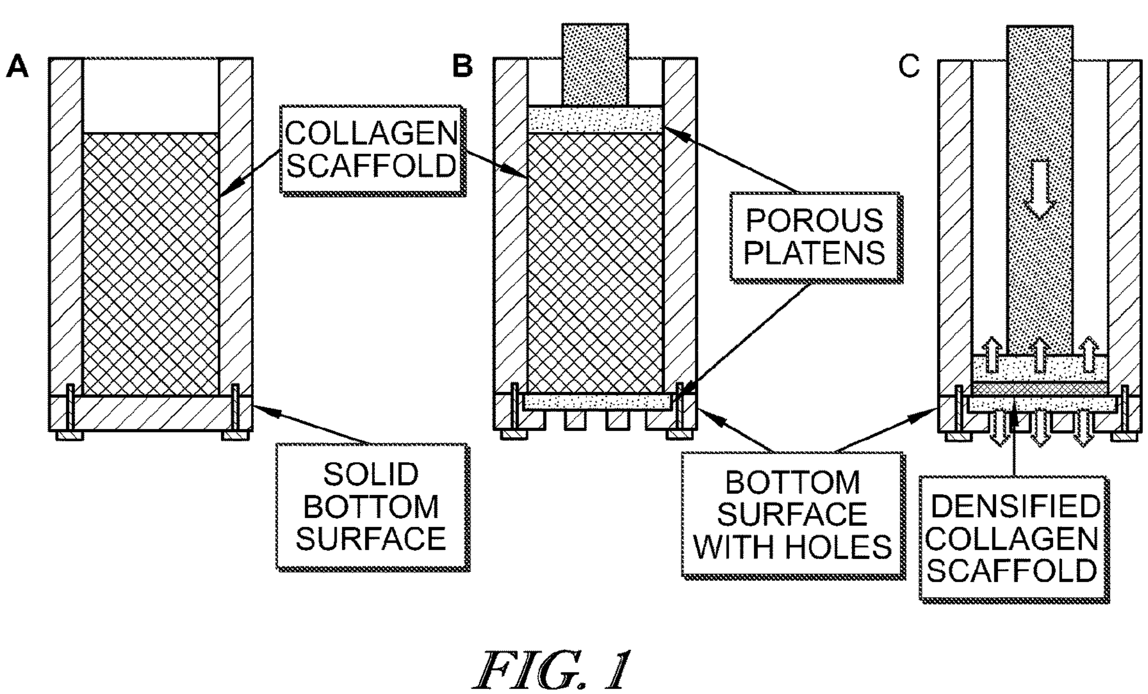
FIG. 1A shows a chamber compression device and associated densification/dehydration process. The cylindrical chamber was made from Delrin with a solid spherical sheet affixed to the bottom. The cylinder was filled with liquid collagen, which is polymerized at 37° C. to form a composite, low density collagen matrix composed of an interconnected network of fibrillar collagen surrounded by interstitial fluid.
FIG. 1B shows that the solid bottom can be removed and replaced with a thin spherical sheet of porous polyethylene foam, which is secured with a porous bottom surface. A thin spherical sheet of porous polyethylene foam can then be placed on the top surface of the collagen scaffold.
FIG. 1C shows that a compressive load can be applied to the upper polyethylene foam in the direction of the grey arrow, driving fluid out of the collagen scaffold via both the upper and lower surfaces (white arrows) to create a hydrated densified collagen scaffold.

The materials and medical grafts described herein comprise engineered collagen scaffolds that can be prepared in a hydrated form or a desiccated (dried) form that can be hydrated. Both can be used for surgical repair, regeneration, restoration, or reconstruction of damaged or dysfunctional tissues, such as pericardium, skin, airway tissue, body wall, and tissue reconstructed following tumor removal, and the like, and for the manufacture of advanced regenerative tissue replacements (e.g., heart valves, such as aortic valves and pulmonic valves, and vascular grafts). The collagen scaffolds described herein persist following implantation in vivo, restoring tissue continuity and maintaining their physical integrity and inducing host tissue integration, cellularization, and site-appropriate tissue regeneration without inducing an inflammatory or a foreign body reaction. In various embodiments, the collagen scaffolds described herein include high-strength, thin, sheet-like materials or high-strength, thin material formats of various shapes with physical and mechanical properties similar to various naturally-occurring high-strength tissues and conventional collagen-based materials.

The terms "restore," "regenerate," "replace," and "repair" as used in reference to tissue refer, respectively, to the reestablishment of a tissue presence in an area of a patient that previously had been characterized by a tissue void or defect and to the regrowth of tissue in this same area. In some embodiments, the restored and/or regenerated and/or repaired tissue may reflect one or more of the appearance, structure, and function of the original tissue that is being replaced.

In one aspect, the invention described herein relates to engineered collagen scaffolds with a thickness of from about 0.005 mm to about 3 mm, and with a high strength (e.g., a high elastic modulus of about 0.5 MPa to about 200 MPa). In one embodiment, the engineered collagen scaffolds can be non-collapsible and/or non-expandable. In another aspect, methods of use of these collagen scaffolds are provided.

In various aspects, the engineered collagen scaffold can have a thickness of from about 0.005 mm to about 3 mm, from about 0.01 mm to about 2.0 mm, from about 0.01 mm to about 1.0 mm, from about 0.01 mm to about 0.25 mm, from about 0.1 mm to about 1.0 mm, from about 0.5 mm to about 1.0 mm, or from about 0.15 mm to about 0.25 mm. In other embodiments, the collagen scaffold can have an elastic modulus of from about 18 MPa to about 200 MPa, from about 20 MPa to about 180 MPa, from about 40 MPa to about 120 MPa, from about 60 MPa to about 100 MPa, or from about 80 MPa to about 180 MPa. In other embodiments, the collagen scaffold can have an ultimate tensile strength of from about 0.5 MPa to about 20 MPa, from about 1 MPa to about 25 MPa, from about 0.2 MPa to about 20 MPa, from about 5 MPa to about 15 MPa, or from about 2 MPa to about 20 MPa. In other illustrative embodiments, the engineered collagen scaffold can have a failure strain of from about 5% to about 70% or from about 10% to about 40%. In other aspects, the engineered collagen scaffold can have a suture retention peak load of from about 2 N to about 8 N, from about 0.2 N to about 2 N, or from about 0.1 N to about 4 N.

In another embodiment, a non-collapsible and/or non-expandable engineered collagen scaffold is provided. The collagen scaffold has a thickness of from about 0.005 mm to about 3 mm and an elastic modulus of from about 0.5 MPa to about 200 MPa. As used herein, the term "non-collapsible" means that the collagen scaffold maintains thickness, and other geometric properties, when transitioned from a dehydrated to a hydrated state. As used herein, the term "non-expandable" means that the material does not expand or swell when lyophilized or rehydrated. Accordingly, in one illustrative embodiment, the collagen scaffold described herein does not collapse when the collagen scaffold is lyophilized and is rehydrated. In one aspect, the collagen scaffold is non-collapsible and/or non-expandable due to its high elastic modulus, which is, in part, determined by fibril density in the collagen scaffold along with hydrophilic (water-retaining) properties.

In yet another embodiment, a method of treating a patient to regenerate, restore, or replace a damaged or a dysfunctional tissue is provided. The method comprises implanting into the patient a medical graft comprising any of the engineered collagen scaffolds described herein. As used herein a "medical graft" means any of the collagen materials described herein which are administered to a patient.

Additional embodiments are also described by the following enumerated clauses. For all of the embodiments described herein, any applicable combination of embodiments is contemplated. Any applicable combination of the embodiments described below is considered to be in accordance with the invention. Any combination of the embodiments described below with the embodiments described in the Background and Summary section, the Detailed Description of the Illustrative Embodiments section, the Examples section, or the claims of this patent application, is considered to be part of the invention.

1. A non-collapsible and/or non-expandable engineered collagen scaffold, wherein the collagen scaffold has a thickness of from about 0.005 mm to about 3 mm and an elastic modulus of from about 0.5 MPa to about 200 MPa.
2. The engineered collagen scaffold of clause 1, wherein the collagen scaffold does not collapse when the collagen scaffold is lyophilized and rehydrated.

3. The engineered collagen scaffold of any one of clauses 1 to 2, wherein the collagen scaffold has a thickness of from about 0.01 mm to about 2.0 mm.
4. The engineered collagen scaffold of any one of clauses 1 to 2, wherein the collagen scaffold has a thickness of from about 0.01 mm to about 1.0 mm.
5. The engineered collagen scaffold of any one of clauses 1 to 2, wherein the collagen scaffold has a thickness of from about 0.01 mm to about 0.25 mm.
6. The engineered collagen scaffold of any one of clauses 1 to 2, wherein the collagen scaffold has a thickness of from about 0.1 mm to about 1.0 mm.
7. The engineered collagen scaffold of any one of clauses 1 to 2, wherein the collagen scaffold has a thickness of from about 0.5 mm to about 1.0 mm.
8. The engineered collagen scaffold of any one of clauses 1 to 2, wherein the collagen scaffold has a thickness of from about 0.15 mm to about 0.25 mm.
9. The engineered collagen scaffold of any one of clauses 1 to 8, wherein the collagen scaffold has an elastic modulus of from about 18 MPa to about 200 MPa.
10. The engineered collagen scaffold of any one of clauses 1 to 8, wherein the collagen scaffold has an elastic modulus of from about 20 MPa to about 180 MPa.
11. The engineered collagen scaffold of any one of clauses 1 to 8, wherein the collagen scaffold has an elastic modulus of from about 40 MPa to about 120 MPa.
12. The engineered collagen scaffold of any one of clauses 1 to 8, wherein the collagen scaffold has an elastic modulus of from about 60 MPa to about 100 MPa.
13. The engineered collagen scaffold of any one of clauses 1 to 8, wherein the collagen scaffold has an elastic modulus of from about 80 MPa to about 180 MPa.
14. The engineered collagen scaffold of any one of clauses 1 to 8, wherein the collagen scaffold has an ultimate tensile strength of from about 0.5 MPa to about 20 MPa.
15. The engineered collagen scaffold of any one of clauses 1 to 8, wherein the collagen scaffold has an ultimate tensile strength of from about 1 MPa to about 25 MPa.
16. The engineered collagen scaffold of any one of clauses 1 to 15, wherein the collagen scaffold has an ultimate tensile strength of from about 0.2 MPa to about 20 MPa.
17. The engineered collagen scaffold of any one of clauses 1 to 15, wherein the collagen scaffold has an ultimate tensile strength of from about 5 MPa to about 15 MPa.
18. The engineered collagen scaffold of any one of clauses 1 to 15, wherein the collagen scaffold has an ultimate tensile strength of from about 2 MPa to about 20 MPa.
19. The engineered collagen scaffold of any one of clauses 1 to 18, wherein the collagen scaffold has a failure strain of from about 5% to about 70%.
20. The engineered collagen scaffold of any one of clauses 1 to 18, wherein the collagen scaffold has a failure strain of from about 10% to about 40%.
21. The engineered collagen scaffold of any one of clauses 1 to 20, wherein the collagen scaffold has a suture retention peak load of from about 2 N to about 8 N.
22. The engineered collagen scaffold of any one of clauses 1 to 20, wherein the collagen scaffold has a suture retention peak load of from about 0.2 N to about 2 N.
23. The engineered collagen scaffold of any one of clauses 1 to 20, wherein the collagen scaffold has a suture retention peak load of from about 0.1 N to about 4 N.
24. The engineered collagen scaffold of any one of clauses 1 to 23, wherein the engineered collagen scaffold is in a composition and the composition further comprises fluid.
25. The engineered collagen scaffold of clause 24, wherein the percentage of fluid present is from about 5% to about 99%.
26. The engineered collagen scaffold of any one of clauses 24 or 25, wherein the composition is dried by lyophilizing the composition, vacuum pressing the composition, or by dehydrothermal treatment, or a combination thereof.
27. The engineered collagen scaffold of any one of clauses 1 to 26, wherein the collagen is Type I collagen.
28. The engineered collagen scaffold of any one of clauses 1 to 27, wherein the collagen is purified Type I collagen.
29. The engineered collagen scaffold of any one of clauses 1 to 28, wherein the engineered collagen scaffold is a medical graft.
30. The engineered collagen scaffold of any one of clauses 1 to 29, wherein the engineered collagen scaffold is a medical graft and the medical graft is used for the regeneration, the restoration, or the replacement of a damaged or a dysfunctional tissue.
31. The engineered collagen scaffold of clause 30, wherein the engineered collagen scaffold is a medical graft for regeneration or replacement or restoration of a tissue selected from pericardium, heart valve, skin, blood vessels, airway tissue, body wall, and tissue reconstructed following tumor removal.
32. The engineered collagen scaffold of any one of clauses 1 to 31, wherein the engineered collagen scaffold is terminally sterilized or prepared aseptically.
33. The engineered collagen scaffold of clause 32 wherein the collagen scaffold is terminally sterilized by a process selected from treatment with glutaraldehyde, gamma irradiation, electron beam irradiation, or ethylene oxide treatment.
34. The engineered collagen scaffold of any one of clauses 1 to 33, wherein the collagen comprises oligomeric collagen, monomeric collagen, telocollagen, or atelocollagen, or a combination thereof.
35. The engineered collagen scaffold of any one of clauses 1 to 34 compressed into a defined shape.
36. The engineered collagen scaffold of clause 35, wherein the shape is a sphere.
37. The engineered collagen scaffold of clause 35, wherein the shape is a tube.
38. The engineered collagen scaffold of clause 35, wherein the shape is a sheet.
39. The engineered collagen scaffold of any one of clauses 35 to 38, wherein the compression is confined compression.
40. The engineered collagen scaffold of any one of clauses 1 to 39, wherein the collagen concentration is from about 50 to about 1000 mg/cm$^3$.
41. The engineered collagen scaffold of any one of clauses 1 to 39, wherein the collagen concentration is from about 50 to about 900 mg/cm$^3$.
42. The engineered collagen scaffold of any one of clauses 1 to 39, wherein the collagen concentration is from about 50 to about 800 mg/cm$^3$.
43. The engineered collagen scaffold of any one of clauses 1 to 39, wherein the collagen concentration is from about 50 to about 700 mg/cm$^3$.

44. The engineered collagen scaffold of any one of clauses 1 to 39, wherein the collagen concentration is from about 50 to about 600 mg/cm$^3$.
45. The engineered collagen scaffold of any one of clauses 1 to 39, wherein the collagen concentration is from about 50 to about 500 mg/cm$^3$.
46. The engineered collagen scaffold of any one of clauses 1 to 39, wherein the collagen concentration is from about 50 to about 400 mg/cm$^3$.
47. The engineered collagen scaffold of any one of clauses 1 to 39, wherein the collagen concentration is from about 50 to about 300 mg/cm$^3$.
48. The engineered collagen scaffold of any one of clauses 1 to 39, wherein the collagen concentration is from about 50 to about 200 mg/cm$^3$.
49. The engineered collagen scaffold of any one of clauses 1 to 48, wherein the engineered collagen scaffold does not induce an inflammatory or a foreign body reaction when implanted into a patient.
50. The engineered collagen scaffold of any one of clauses 1 to 49 wherein the collagen is selected from pig collagen, human collagen, and bovine collagen.
51. The engineered collagen scaffold of any one of clauses 1 to 49, wherein the collagen is synthetic collagen.
52. The engineered collagen scaffold of any one of clauses 1 to 50, wherein the collagen is native collagen.
53. The engineered collagen scaffold of any one of clauses 1 to 49, wherein the collagen is recombinant collagen.
54. The engineered collagen scaffold of any one of clauses 1 to 53 further comprising cells.
55. The engineered collagen scaffold of clause 54, wherein the cells are stem cells.
56. A method of treating a patient to regenerate, restore, or replace a damaged or a dysfunctional tissue, the method comprising implanting into the patient a medical graft comprising the engineered collagen scaffold of any one of clauses 1 to 55.
57. The method of clause 56, wherein the medical graft is for the regeneration, restoration, or replacement of damaged or dysfunctional pericardium.
58. The method of clause 56, wherein the medical graft is for the regeneration, restoration, or replacement of damaged or dysfunctional heart valve.
59. The method of clause 56, wherein the medical graft is for the regeneration, restoration, or replacement of damaged or dysfunctional skin.
60. The method of clause 59, wherein the valve tissue is aortic valve tissue or pulmonic valve tissue.
61. The engineered collagen scaffold of any one of clauses 1 to 55 or the method of any one of clauses 56 to 60 wherein the engineered collagen scaffold is exogenously cross-linked.
62. The engineered collagen scaffold or the method of clause 61 wherein the engineered collagen scaffold is cross-linked with glutaraldehyde.

As described herein, an "engineered collagen scaffold" or a "collagen scaffold" may refer to a collagen composition that can be synthesized ex-vivo or upon implantation into the body of a patient, to form a collagen fibril-containing scaffold or other collagen structures or materials. In one embodiment, the polymerization can occur under controlled conditions, wherein the controlled conditions include, but are not limited to, pH, phosphate concentration, temperature, buffer composition, ionic strength, and composition and concentration of the extracellular matrix components (e.g., collagen and non-collagenous molecules, if non-collagenous ECM components are included). The "engineered collagen scaffold" is a non-natural collagen scaffold or is another non-natural collagen structure or material.

In one embodiment, the engineered collagen scaffolds of the present disclosure are made using compression techniques. As used herein, the term "compressed" refers to a reduction in size or an increase in density when a force is applied to a collagen scaffold composition. For example, compression can be achieved through various methods of applying force, such as, but not limited to, confined compression, variable compression, physical compression, centrifugation, ultracentrifugation, evaporation or aspiration, and the like.

In one embodiment, the compression is a variable compression. As used herein, the phrase "variable compression" refers to compression of collagen by applying force in a non-linear fashion.

In yet another embodiment, the compression is a physical compression. As used herein, the phrase "physical compression" refers to compression of collagen by applying force by physical means. For embodiments in which the compression is a physical compression, the physical compression can be performed in a chamber comprising an adjustable mold and platen (see, for example, FIG. 1). Typically, collagen may be inserted into the mold and then subjected to compression.

Furthermore, in various embodiments, the physical compression can be varied depending on the placement of the porous platen within the mold. For example, the mold may be adjustable so that porous polyethylene is positioned as part of the platen and/or along the walls or bottom of the sample mold. In some embodiments, the compression is a physical force from at least one direction. In other embodiments, the compression is a physical force from two or more directions. In yet other embodiments, the compression is a physical force from three or more directions. In some embodiments, the compression is a physical force from four or more directions.

In other embodiments, the compression is centrifugation. In other embodiments, the compression is ultracentrifugation. In yet other embodiments, the compression is evaporation. In some embodiments, the compression is aspiration. In certain embodiments, the aspiration is vacuum aspiration.

In some embodiments of the present disclosure, the collagen is solubilized from tissue. For example, the collagen can be prepared by utilizing acid-solubilized collagen and defined polymerization conditions that are controlled to yield three-dimensional collagen scaffolds with a range of controlled assembly kinetics (e.g., polymerization half-time), molecular compositions, and fibril microstructure-mechanical properties, for example, as described in U.S. patent application Ser. No. 11/435,635 (published Nov. 22, 2007, as Publication No. 2007-0269476 A1) and Ser. No. 11/903,326 (published Oct. 30, 2008, as Publication No. 2008-0268052), each incorporated herein by reference in its entirety. In other embodiments, the collagen is polymerizable collagen. In yet another embodiment, the collagen is Type I collagen. In still another embodiment, the collagen is purified Type I collagen.

In some embodiments, the engineered collagen scaffold is a medical graft. In other embodiments, the engineered collagen scaffold can be used to fabricate a regenerative tissue replacement. In other embodiments, the engineered collagen scaffold may be used in vitro. For example, in vitro use of the engineered collagen scaffolds of the present disclosure may be utilized for research purposes such as cell tissue culture, drug discovery, and drug toxicity testing.

In some embodiments, the collagen is unnatural collagen. As used herein, the phrase "unnatural collagen" refers to collagen that has been removed from a source tissue. In one embodiment, the unnatural collagen removed from a source tissue can be native collagen. In one aspect, the unnatural collagen may be solubilized from the tissue source. In other embodiments, the collagen is synthetic collagen. In yet other embodiments, the collagen is recombinant collagen.

In one aspect, unnatural collagen or collagen components can be used and can be obtained from a number of sources, including for example, porcine skin, human skin, or bovine skin, to construct the collagen scaffolds described herein. Suitable tissues useful as a collagen-containing source material for isolating collagen or collagen components to make the collagen scaffolds described herein are submucosa tissues or any other extracellular matrix-containing tissues of a warm-blooded vertebrate. Suitable methods of preparing submucosa tissues are described in U.S. Pat. Nos. 4,902,508, 5,281,422, and 5,275,826, each incorporated herein by reference. In another embodiment, extracellular matrix material-containing tissues other than submucosa tissue may be used to obtain collagen in accordance with the methods and scaffolds described herein. Methods of preparing other extracellular matrix material-derived tissues for use in obtaining purified collagen or partially purified extracellular matrix components are known to those skilled in the art. For example, see U.S. Pat. No. 5,163,955 (pericardial tissue); U.S. Pat. No. 5,554,389 (urinary bladder submucosa tissue); U.S. Pat. No. 6,099,567 (stomach submucosa tissue); U.S. Pat. No. 6,576,265 (extracellular matrix tissues generally); U.S. Pat. No. 6,793,939 (liver basement membrane tissues); and U.S. patent application publication no. US-2005-0019419-A1 (liver basement membrane tissues); and International Publication No. WO 2001/45765 (extracellular matrix tissues generally), each incorporated herein by reference. In various other embodiments, the collagen-containing source material can be selected from the group consisting of placental tissue, ovarian tissue, uterine tissue, animal tail tissue, and skin tissue. In some embodiments, the collagen is selected from the group consisting of pig collagen, bovine collagen, and human collagen. Any suitable extracellular matrix-containing tissue can be used as a collagen-containing source material to isolate purified collagen or to isolate partially purified extracellular matrix components.

An illustrative preparation method for preparing submucosa tissues as a source of purified collagen or partially purified extracellular matrix components is described in U.S. Pat. No. 4,902,508, the disclosure of which is incorporated herein by reference. In one embodiment, a segment of vertebrate intestine, for example, preferably harvested from porcine, ovine or bovine species, but not excluding other species, is subjected to abrasion using a longitudinal wiping motion to remove cells or cell-removal is accomplished by hypotonic or hypertonic lysis. In one embodiment, the submucosa tissue is rinsed under hypotonic conditions, such as with water or with saline under hypotonic conditions and is optionally sterilized. In another illustrative embodiment, such compositions can be prepared by mechanically removing the luminal portion of the tunica mucosa and the external muscle layers and/or lysing resident cells with hypotonic or hypertonic washes, such as with water or saline. In these embodiments, the submucosa tissue can be stored in a hydrated or dehydrated state prior to isolation of the purified collagen or partially purified extracellular matrix components. In various aspects, the submucosa tissue can comprise any delamination embodiment, including the tunica submucosa delaminated from both the tunica muscularis and at least the luminal portion of the tunica mucosa of a warm-blooded vertebrate.

In some embodiments, the collagen is oligomeric collagen. Unlike conventional monomeric collagen preparations, namely telocollagen and atelocollagen, oligomer can represent small aggregates of full-length triple-helical collagen molecules (i.e., tropocollagen) with carboxy- and amino-terminal telopeptide intact, held together by a naturally-occurring intermolecular crosslink. The preservation of these molecular features, including carboxy- and amino-terminal telopeptide regions and associated intermolecular crosslinks, provides this biologic polymer and the collagen materials it forms with desirable but uncommon properties. More specifically, oligomer retains its fibril-forming (self-assembly) capacity, which is inherent to fibrillar collagen proteins. The presence of oligomeric collagen can enhance the self-assembly potential by increasing the assembly rate and by yielding collagen compositions with distinct fibril microstructures and increased mechanical integrity (e.g., stiffness). In some embodiments, the collagen comprises oligomeric collagen. In other embodiments, the collagen consists essentially of oligomeric collagen. In yet other embodiments, the collagen consists of oligomeric collagen.

In some embodiments, the collagen is monomeric collagen. In some embodiments, the collagen is atelocollagen. As used herein, the term "atelocollagen" refers to collagen that is treated in vitro with pepsin or another suitable protease or agent to eliminate or substantially reduce telopeptide regions which contain intermolecular cross-linking sites. In other embodiments, the monomeric collagen is telocollagen. As used herein, the term "telocollagen" refers to acid solubilized collagen that retains its telopeptide ends.

In certain embodiments, the collagen comprises oligomeric collagen and atelocollagen. In other embodiments, the collagen comprises oligomeric collagen, monomeric collagen, and atelocollagen. The amounts of oligomeric collagen, monomeric collagen, and/or atelocollagen may be formulated in the collagen scaffold compositions to advantageously maximize the stiffness, strength, fluid and mass transport, proteolytic degradation or compatibility of the engineered collagen scaffolds.

In any of the embodiments described herein, the engineered collagen scaffolds can have a predetermined percentage of collagen oligomers. In various embodiments, the predetermined percentage of collagen oligomers can be from about 0.5% to about 100%, from about 30% to about 100%, from about 40% to about 100%, from about 50% to about 100%, from about 60% to about 100%, from about 70% to about 100%, from about 80% to about 100%, from about 90% to about 100%, from about 95% to about 100%, or about 100%. In yet another embodiment, the collagen oligomers are obtained from a collagen-containing source material enriched with collagen oligomers (e.g., pig skin).

In any of the embodiments described herein, the engineered collagen scaffolds can have an oligomer content quantified by average polymer molecular weight (AMW). As described herein, modulation of AMW can affect polymerization kinetics, fibril microstructure, molecular properties, and fibril architecture of the collagen scaffolds, for example, interfibril branching, pore size, and mechanical integrity (e.g., scaffold stiffness). In another embodiment, the oligomer content of the purified collagen, as quantified by average polymer molecular weight, positively correlates with scaffold stiffness.

In some embodiments, the collagen is thermoreversible collagen. As used herein "thermoreversible collagen" means collagen that can reversibly transition between solution and matrix phases in response to temperature modulation between 4° C. and 37° C. or temperature modulation between any other temperatures that cause reversible matrix to solution transitions.

In some embodiments, the collagen is reduced collagen. As used herein "reduced collagen" means collagen that is reduced in vitro to eliminate or substantially reduce reactive aldehydes. For example, collagen may be reduced in vitro by treatment of collagen with a reducing agent (e.g., sodium borohydride).

In some embodiments, the collagen is oligomer 260 collagen. As used herein "oligomer 260 collagen" is a collagen preparation made (e.g., from porcine skin), by procedures resulting in isolation of oligomers, where the collagen preparation has a prominent band at molecular weight 260, where the band is not prominent or is lacking in corresponding monomer preparations. The presence of the band can be determined by SDS polyacrylamide gel electrophoresis. Oligomer 260 collagen is further described U.S. patent application Ser. No. 13/192,276 (published Feb. 2, 2012, as Publication No. 2012-0027732 A1), incorporated herein by reference.

In other illustrative embodiments, the engineered collagen scaffolds described herein may be cross-linked using cross-linking agents, such as glutaraldehyde, carbodiimides, aldehydes, lysl-oxidase, N-hydroxysuccinimide esters, imidoesters, hydrazides, and maleimides, and the like, or combinations thereof, for example. In one aspect, the cross-linking agent(s) can be added before, during, or after polymerization of the collagen in the engineered collagen scaffold.

The concentration of collagen present in the various engineered collagen scaffold embodiments of the present disclosure may vary. In some embodiments, the collagen is present in the engineered collagen scaffold at a concentration of from about 50 to about 1000 mg/cm$^3$, from about 50 to about 900 mg/cm$^3$, from about 50 to about 800 mg/cm$^3$, from about 50 to about 700 mg/cm$^3$, from about 50 to about 600 mg/cm$^3$, from about 50 to about 500 mg/cm$^3$, from about 50 to about 400 mg/cm$^3$, from about 50 to about 300 mg/cm$^3$, from about 50 to about 200 mg/cm$^3$, from about 100 to about 1000 mg/cm$^3$, from about 100 to about 900 mg/cm$^3$, from about 100 to about 800 mg/cm$^3$, from about 100 to about 700 mg/cm$^3$, from about 100 to about 600 mg/cm$^3$, from about 100 to about 500 mg/cm$^3$, from about 100 to about 400 mg/cm$^3$, from about 100 to about 300 mg/cm$^3$, from about 100 to about 200 mg/cm$^3$, from about 200 to about 1000 mg/cm$^3$, from about 200 to about 900 mg/cm$^3$, from about 200 to about 800 mg/cm$^3$, from about 200 to about 700 mg/cm$^3$, from about 200 to about 600 mg/cm$^3$, from about 200 to about 500 mg/cm$^3$, from about 200 to about 400 mg/cm$^3$, from about 200 to about 300 mg/cm$^3$, from about 300 to about 1000 mg/cm$^3$, from about 300 to about 900 mg/cm$^3$, from about 300 to about 800 mg/cm$^3$, from about 300 to about 700 mg/cm$^3$, from about 300 to about 600 mg/cm$^3$, from about 300 to about 500 mg/cm$^3$, from about 300 to about 400 mg/cm$^3$, from about 400 to about 1000 mg/cm$^3$, from about 400 to about 900 mg/cm$^3$, from about 400 to about 800 mg/cm$^3$, from about 400 to about 700 mg/cm$^3$, from about 400 to about 600 mg/cm$^3$, from about 400 to about 500 mg/cm$^3$, from about 500 to about 1000 mg/cm$^3$, from about 500 to about 900 mg/cm$^3$, from about 500 to about 800 mg/cm$^3$, from about 500 to about 700 mg/cm$^3$, from about 500 to about 600 mg/cm$^3$, from about 50 to about 2000 mg/cm$^3$, or from about 50 to about 1500 mg/cm$^3$.

In other embodiments, the collagen can be present in the starting composition used to polymerize the collagen, to make the collagen scaffold, at from about 1 mg/ml to about 50 mg/ml, from about 1 mg/ml to about 40 mg/ml, from about 1 mg/ml to about 30 mg/ml, from about 1 mg/ml to about 20 mg/ml, from about 1 mg/ml to about 15 mg/ml, from about 1 mg/ml to about 12 mg/ml, from about 1 mg/ml to about 10 mg/ml, from about 1 mg/ml to about 9 mg/ml, from about 1 mg/ml to about 8 mg/ml, from about 1 mg/ml to about 7 mg/ml, from about 1 mg/ml to about 6 mg/ml, from about 1 mg/ml to about 5 mg/ml, from about 1 mg/ml to about 4 mg/ml, or from about 1 mg/ml to about 3 mg/ml.

In some embodiments, the collagen scaffold further comprises a polymer. As used herein, the term "polymer" refers to a molecule consisting of individual chemical moieties, which may be the same or different, but are preferably the same, that are joined together. As used herein, the term "polymer" refers to individual chemical moieties that are joined end-to-end to form a linear molecule, as well as individual chemical moieties joined together in the form of a branched (e.g., a "multi-arm" or "star-shaped") structure. In other embodiments, the collagen scaffold further comprises a co-polymer. As used herein, the term "co-polymer" refers to a polymer derived from more than one species of monomer, including copolymers that may be obtained by copolymerization of two monomer species, those that may be obtained from three monomers species ("terpolymers"), those that may be obtained from four monomers species ("quaterpolymers"), etc.

In various embodiments of the present disclosure, the collagen scaffolds as described herein may be polymerized under controlled conditions to obtain particular physical properties. For example, the collagen scaffolds may have desired collagen fibril density, pore size (fibril-fibril branching), elastic modulus, tensile strain, tensile stress, linear modulus, compressive modulus, ultimate tensile strength, failure strain, suture retention peak load, loss modulus, fibril area fraction, fibril volume fraction, collagen concentration, cell seeding density, shear storage modulus (G' or elastic (solid-like) behavior), and phase angle delta (δ or the measure of the fluid (viscous)- to solid (elastic)-like behavior; δ equals 0° for Hookean solid and 90° for Newtonian fluid).

As used herein, a "modulus" can be an elastic or linear modulus (defined by the slope of the linear region of the stress-strain curve obtained using conventional mechanical testing protocols; i.e., stiffness), a compressive modulus, a loss modulus, or a shear storage modulus (e.g., a storage modulus). These terms are well-known to those skilled in the art.

As used herein, a "fibril volume fraction" (i.e., fibril density) is defined as the percent area of the total area occupied by fibrils in three dimensions.

As used herein, tensile or compressive stress "a" is the force carried per unit of area and is expressed by the equation:

$$\sigma = \frac{P}{A}$$

where σ=stress, P=force, and A=cross-sectional area.

The force (P) produces stresses normal (i.e., perpendicular) to the cross section of the material (e.g., if the stress tends to lengthen the material, it is called tensile stress, and if the stress tends to shorten the material, it is called compressive stress).

As used herein, "strain" refers to mechanical strain which is the deformation to a material as a result of mechanical stresses. Strains are routinely defined as the ratio of displacements divided by reference lengths. As used herein, "tensile strain" is the elongation of the material which is subjected to tension.

In any embodiment described herein, the fibril volume fraction of the collagen scaffold can be from about 1% to about 60%. In various embodiments, the collagen scaffold can contain fibrils with specific characteristics, for example, a fibril volume fraction (i.e., density) of from about 2% to about 90%, from about 2% to about 80%, from about 2% to about 70%, from about 2% to about 60%, from about 2% to about 50%, from about 2% to about 40%, from about 5% to about 60%, from about 15% to about 60%, from about 2% to about 30%, from about 5% to about 30%, from about 15% to about 30%, from about 20% to about 30%, from about 5% to about 90%, from about 15% to about 90%, from about 2% to about 80%, from about 5% to about 80%, from about 15% to about 80%, or from about 20% to about 80%.

In any of the illustrative embodiments described herein, the collagen scaffold can contain fibrils with specific characteristics, including, but not limited to, a modulus (e.g., a compressive modulus, loss modulus, elastic modulus, or a storage modulus) of from about 18 MPa to about 200 MPa, of from about 20 MPa to about 200 MPa, of from about 20 MPa to about 180 MPa, of from about 20 MPa to about 170 MPa, of from about 20 MPa to about 160 MPa, of from about 20 MPa to about 150 MPa, of from about 20 MPa to about 140 MPa, of from about 20 MPa to about 130 MPa, of from about 20 MPa to about 120 MPa, of from about 20 MPa to about 110 MPa, of from about 20 MPa to about 100 MPa, of from about 20 MPa to about 90 MPa, of from about 20 MPa to about 80 MPa, of from about 20 MPa to about 70 MPa, of from about 20 MPa to about 60 MPa, of from about 20 MPa to about 50 MPa, of from about 20 MPa to about 40 MPa, of from about 20 MPa to about 30 MPa, or of from about 20 MPa to about 25 MPa. In other embodiments the collagen scaffold can have an elastic modulus of from about 0.5 MPa to about 200 MPa, of from about 0.5 MPa to about 190 MPa, of from about 0.5 MPa to about 180 MPa, of from about 0.5 MPa to about 170 MPa, of from about 0.5 MPa to about 160 MPa, of from about 0.5 MPa to about 150 MPa, of from about 0.5 MPa to about 140 MPa, of from about 0.5 MPa to about 130 MPa, of from about 0.5 MPa to about 120 MPa, of from about 0.5 MPa to about 110 MPa, of from about 0.5 MPa to about 105 MPa, of from about 0.5 MPa to about 100 MPa, of from about 0.5 MPa to about 90 MPa, of from about 0.5 MPa to about 80 MPa, of from about 0.5 MPa to about 70 MPa, of from about 0.5 MPa to about 60 MPa, of from about 0.5 MPa to about 50 MPa, of from about 0.5 MPa to about 40 MPa, of from about 0.5 MPa to about 30 MPa, of from about 0.5 MPa to about 20 MPa, of from about 0.5 MPa to about 10 MPa, of from about 0.5 MPa to about 5 MPa, or of from about 0.5 MPa to about 1 MPa.

In any of the embodiments described herein, the collagen composition can contain fibrils with specific characteristics, including, but not limited to, a phase angle delta (δ) of from about 0° to about 12°, from about 0° to about 5°, from about 1° to about 5°, from about 4° to about 12°, from about 5° to about 7°, from about 8° to about 10°, and from about 5° to about 10°.

In various aspects, the engineered collagen scaffold can have a thickness of from about 0.005 to about 3 mm, from about 0.005 to about 2 mm, from about 0.005 to about 1 mm, from about 0.005 to about 0.5 mm, from about 0.01 mm to about 3.0 mm, from about 0.01 mm to about 2.0 mm, from about 0.01 mm to about 1.0 mm, from about 0.01 mm to about 0.5 mm, from about 0.01 mm to about 0.25 mm, from about 0.1 mm to about 1.0 mm, from about 0.5 mm to about 1.0 mm, from about 0.15 mm to about 0.25 mm, from about 0.02 mm to about 0.2 mm, from about 0.02 mm to about 0.15 mm, or from about 0.02 mm to about 0.1 mm.

In other embodiments, the collagen scaffold can have an ultimate tensile strength of from about 0.5 MPa to about 20 MPa, from about 1 MPa to about 25 MPa, from about 0.2 MPa to about 20 MPa, from about 5 MPa to about 15 MPa, from about 2 MPa to about 20 MPa, from about 1 MPa to about 20, from about 1 MPa to about 15 MPa, from about 1 MPa to about 10 MPa, from about 1 MPa to about 5 MPa, from about 1 MPa to about 4 MPa, from about 1 MPa to about 3 MPa, from about 1 MPa to about 2 MPa, from about 0.5 MPa to about 25 MPa, from about 0.5 MPa to about 20, from about 0.5 MPa to about 15 MPa, from about 0.5 MPa to about 10 MPa, from about 0.5 MPa to about 5 MPa, from about 0.5 MPa to about 4 MPa, from about 0.5 MPa to about 3 MPa, from about 0.5 MPa to about 2 MPa, or from about 0.5 MPa to about 1 MPa.

In other illustrative embodiments, the engineered collagen scaffold can have a failure strain of from about 5% to about 70%, of from about 5% to about 60%, of from about 5% to about 50%, of from about 5% to about 40%, of from about 5% to about 30%, of from about 5% to about 20%, of from about 5% to about 10%, of from about 10% to about 70%, of from about 10% to about 60%, of from about 10% to about 50%, of from about 10% to about 40%, of from about 10% to about 30%, or of from about 10% to about 20%.

In other aspects, the engineered collagen scaffold can have a suture retention peak load of from about 2 N to about 8 N, from about 0.2 N to about 2 N, or from about 0.1 N to about 4 N, of from about 2 N to about 7 N, of from about 2 N to about 6 N, of from about 2 N to about 5 N, of from about 2 N to about 4 N, of from about 2 N to about 3 N, of from about 0.1 N to about 8 N, of from about 0.1 N to about 7 N, of from about 0.1 N to about 6 N, of from about 0.1 N to about 5 N, of from about 0.1 N to about 4 N, of from about 0.1 N to about 3 N, of from about 0.1 N to about 2 N, of from about 0.1 N to about 1 N, of from about 0.2 N to about 8 N, of from about 0.2 N to about 7 N, of from about 0.2 N to about 6 N, of from about 0.2 N to about 5 N, of from about 0.2 N to about 4 N, of from about 0.2 N to about 3 N, of from about 0.2 N to about 2 N, of from about 0.2 N to about 1 N, or of from about 0.2 N to about 0.5 N.

In all of the embodiments described herein, "from about" "to about" includes the numbers referred to at each end of the range. For example, "from about 20% to about 80%" includes 20% and 80%, "from about 20 MPa to about 200 MPa" includes 20 and 200 MPa, etc. As used herein, "about" in reference to a numeric value, including, for example, whole numbers, fractions, and percentages, generally refers to a range of numerical values (e.g., +/−5% to 10% of the recited value) that one of ordinary skill in the art would consider equivalent to the recited value (e.g., having the same function or result).

In any of the illustrative embodiments described herein, qualitative and quantitative microstructural characteristics of the collagen scaffolds can be determined by cryostage scanning electron microscopy, transmission electron microscopy, confocal microscopy, or second harmonic generation multi-photon microscopy, and the like. In another embodiment, tensile, compressive and viscoelastic properties can be determined by rheometry or tensile testing. All of these methods are known in the art or are further described in U.S. patent application Ser. No. 11/435,635 (published Nov. 22, 2007, as Publication No. 2007-0269476 A1), U.S. patent application Ser. No. 11/914,606 (published Jan. 8, 2009, as Publication No. 2009-0011021 A1), U.S. patent application Ser. No. 12/300,951 (published Jul. 9, 2009, as Publication No. 2009-0175922 A1), U.S. patent application Ser. No. 13/192,276 (published Feb. 2, 2012, as Publication No. 2012-0027732 A1), U.S. patent application Ser. No. 13/383,796 (published May 10, 2012, as Publication No. 2012-0115222 A1), or are described in Roeder et al., *J. Biomech. Eng.*, vol. 124, pp. 214-222 (2002), in Pizzo et al., *J. Appl. Physiol.*, vol. 98, pp. 1-13 (2004), Fulzele et al., *Eur. J. Pharm. Sci.*, vol. 20, pp. 53-61 (2003), Griffey et al., *J. Biomed. Mater. Res.*, vol. 58, pp. 10-15 (2001), Hunt et al., *Am. J. Surg.*, vol. 114, pp. 302-307 (1967), and Schilling et al., *Surgery*, vol. 46, pp. 702-710 (1959), incorporated herein by reference.

In various embodiments, the collagen scaffold composition further comprises cells. Any cell type within the knowledge of a person of ordinary skill in the art can be used with the collagen scaffold compositions of the present disclosure. In some embodiments, the cells are stem cells. As used herein, "stem cell" refers to an unspecialized cell from an embryo, fetus, or adult that is capable of self-replication or self-renewal and can develop into a variety of specialized cell types (i.e., potency). The term as used herein, unless further specified, encompasses oligopotent cells (those cells that can differentiate into a few cell types, e.g., lymphoid or myeloid lineages), and unipotent cells (those cells that can differentiate into only one cell type). In some embodiments, hematopoietic stem cells may be isolated from, for example, bone marrow, circulating blood, or umbilical cord blood by methods well-known to those skilled in the art. A cell marker can be used to select and purify the hematopoietic stem cells. For example, suitable markers are the Lin−, Sca1+, and c-Kit+ mouse or Lin−, CD34+, and c-Kit+ human hematopoietic stem cell markers. In one embodiment, cell markers may be used alone or in combination to select and purify the desired cell type for use in the compositions and methods herein described. In one aspect, the collagen scaffold composition can be seeded with autogenous cells isolated from the patient to be treated. In an alternative embodiment, the cells may be xenogeneic or allogeneic in nature.

In any of the embodiments described herein, the cells are seeded on the collagen scaffold composition at a cell density of from about $1\times10^6$ to about $1\times10^8$ cells/ml, or at a density of from about $1\times10^3$ to about $2\times10^6$ cells/ml. In one embodiment cells are seeded at a density of less than $5\times10^4$ cells/ml. In another embodiment cells are seeded at a density of less than $1\times10^4$ cells/ml. In another embodiment, cells are seeded at a density selected from a range of about $1\times10^2$ to about $5\times10^6$, from about $0.3\times10^4$ to about $60\times10^4$ cells/ml, and from about $0.5\times10^4$ to about $50\times10^4$ cells/ml. The cells are maintained, proliferated, or differentiated according to methods described herein or to methods well-known to the skilled artisan for cell culture.

In any of the various embodiments described herein, the engineered collagen scaffold compositions of the present invention can be combined, prior to, during, or after polymerization, with nutrients, including minerals, amino acids, sugars, peptides, proteins, vitamins (such as ascorbic acid), or glycoproteins that facilitate hematopoietic stem cell culture or the culture of other types of cells, such as laminin and fibronectin, hyaluronic acid, or growth factors such as platelet-derived growth factor, or transforming growth factor beta, and glucocorticoids such as dexamethasone. In other illustrative embodiments, fibrillogenesis inhibitors, such as glycerol, glucose, or polyhydroxylated compounds can be added prior to or during polymerization. In accordance with one embodiment, cells can be added to the collagen scaffolds and other extracellular matrix components as the last step prior to the polymerization or after polymerization of the collagen. In other illustrative embodiments, cross-linking agents, such as carbodiimides, aldehydes, lysl-oxidase, N-hydroxysuccinimide esters, imidoesters, hydrazides, and maleimides, and the like can be added before, during, or after collagen polymerization. In yet another embodiment, the engineered collagen scaffold compositions can include components such as a buffer (e.g., phosphate-buffered saline), hydrochloric acid (e.g., 0.01N), and glucose. In one aspect, glucose can be added if cells are to be included. In another embodiment, non-collagenous components of the ECM, normally present in natural collagen matrices, are not present.

In certain embodiments, the collagen scaffold composition further comprises fluid. Although some fluid is removed from the collagen scaffold compositions pursuant to compression, an amount of fluid is retained in the compressed collagen scaffold compositions. In some embodiments, the percentage of fluid present is from about 25% to about 99%, from about 5% to about 99%, from about 5% to about 95%, from about 5% to about 90%, from about 5% to about 80%, from about 5% to about 70%, from about 5% to about 60%, from about 5% to about 50%, from about 5% to about 40%, or from about 5% to about 30%, from about 10% to about 99%, from about 10% to about 90%, from about 10% to about 80%, from about 10% to about 70%, from about 10% to about 60%, from about 10% to about 50%, from about 10% to about 40%, from about 10% to about 30%, or from about 10% to about 20%. In some embodiments, the percentage of fluid present is from about 20% to about 99%, from about 30% to about 99%, from about 40% to about 99%, from about 45% to about 99%, from about 50% to about 99%, from about 60% to about 99%, from about 70% to about 99%, or from about 80% to about 99%. In some embodiments, the percentage of fluid present is from about 50% to about 80%. In some embodiments, the percentage of fluid present is from about 60% to about 70%.

In various embodiments, the collagen scaffold composition is lyophilized. As used herein, the term "lyophilized" relates to the removal of water from a composition, typically by freeze-drying under a vacuum. However, desiccation can be performed by any method known to the skilled artisan and the method is not limited to freeze-drying under a vacuum. Typically, the lyophilized collagen scaffold composition is lyophilized to dryness, and in one embodiment the water content of the lyophilized collagen scaffold composition is below detectable levels. In another embodiment, the collagen scaffold can be dried by lyophilizing the composition, vacuum pressing the composition, or by dehydrothermal treatment, or a combination thereof.

In another embodiment provided herein, a method of treating a patient to regenerate, restore, or replace a damaged or a dysfunctional tissue is provided. The method comprises implanting into the patient a medical graft comprising any of the engineered collagen scaffolds described herein. In various embodiments, the medical graft can be for regeneration or replacement or restoration of a tissue selected from pericardium, heart value, skin, blood vessels, airway tissue, body wall, and tissue reconstructed following tumor removal tissue. In another embodiment, the valve tissue can be aortic or pulmonic valve tissue. In one embodiment, the medical graft (i.e., the collagen scaffold) does not induce an inflammatory or a foreign body reaction when implanted into the patient.

In one aspect, the engineered collagen scaffold is terminally sterilized or is prepared aseptically before implantation into the patient. In various embodiments, terminal sterilization methods can be processes selected from treatment with glutaraldehyde, gamma irradiation, electron beam irradiation, peracetic acid sterilization, formaldehyde tanning at acidic pH, propylene oxide, ethylene oxide treatment, or gas plasma sterilization. Sterilization techniques which do not adversely affect the structure of the collagen can be used.

In another embodiment provided herein, a method of manufacturing an engineered collagen scaffold by compression, such as confined compression, is provided. Any of the embodiments of the engineered collagen scaffolds described herein can be produced by the method of manufacturing. In some embodiments, the method of manufacturing comprises the step of polymerizing the collagen prior to compressing the collagen scaffold composition into a defined shape. In certain embodiments, the method of manufacturing comprises the step of tuning a physical property of the collagen scaffold prior to compressing the collagen scaffold composition into a defined shape. As used herein, the term "tuning" refers to modification of the collagen scaffold under controlled conditions to obtain a desired physical property. For example, prior to compression, the collagen scaffold can be modified under controlled conditions to provide a desired value or quantity of one or more of the following physical properties: fibril density, pore size (fibril-fibril branching), elastic modulus, thickness, tensile strain, tensile stress, linear modulus, ultimate tensile stress, failure strain, suture retention peak load, compressive modulus, loss modulus, fibril area fraction, fibril volume fraction, collagen concentration, cell seeding density, shear storage modulus (G' or elastic (solid-like) behavior), and phase angle delta (δ or the measure of the fluid (viscous)- to solid (elastic)-like behavior; δ equals 0° for Hookean solid and 90° for Newtonian fluid).

As a result of tuning the physical property prior to compressing the collagen scaffold composition, a high level interfibril association may be introduced to the collagen scaffold prior to compression. This step allows for control of important mechanical properties prior to creation of the final collagen scaffold, and the controlled mechanical properties are retained following compression of the final collagen scaffold. Therefore, design features of collagen scaffolds can be optimized for purposes of predictably inducing desired cellular mechanisms into the collagen scaffolds.

The collagen scaffolds described herein can be compressed into a number of different defined shapes. In some embodiments, the defined shape is a tube. In other embodiments, the defined shape is a sheet. In yet other embodiments, the defined shape is a sphere. In some embodiments, the defined shape is a slab. In other embodiments, the defined shape is a cylinder. In yet other embodiments, the defined shape is a cone.

In another embodiment, the methods, uses, and collagen scaffolds and collagen scaffold compositions described herein include the following examples. The examples further illustrate additional features of the various embodiments of the invention described herein. However, it is to be understood that the examples are illustrative and are not to be construed as limiting other embodiments of the invention described herein. In addition, it is appreciated that other variations of the examples are included in the various embodiments of the invention described herein.

Example 1

Formation of Hydrated Collagen Scaffolds by Compression Dehydration

Chamber Compression System:

Type I oligomeric collagen was isolated and purified from porcine dermis. Hides were obtained from closed-herd, market-weight barrows located within the United States and certified free of infectious or contagious diseases. Acid-solubilized collagen oligomer was sterile filtered and quality controlled based on purity, molecular composition, and polymerization parameters. Densified collagen scaffolds were created aseptically using a customized confined compression procedure using cylindrical chambers fabricated from Delrin (FIG. 1). The bottom surface of these chambers was removable to accommodate the two configurations: 1) a solid bottom surface to contain liquid collagen prior to and during polymerization (FIG. 1A) and 2) a porous bottom surface with holes to facilitate controlled fluid removal from the bottom during compression (FIGS. 1B and C). To create collagen scaffolds, liquid collagen at specified concentrations and volumes was neutralized and added to sterile cylindrical chambers (either 6.3 cm or 3.4 cm diameter) (FIG. 1A). These chambers were sealed and incubated at 37° C. to induce collagen polymerization resulting in the formation of a composite collagen scaffold comprising a network of fibrillar collagen surrounded by interstitial fluid. After, collagen polymerization, sterile porous polyethylene foam was placed on top and bottom surfaces of the composite collagen scaffold, and the solid bottom surface of the chamber was changed to the porous bottom surface (FIG. 1B). The collagen was then compressed at a strain rate of 0.05% per second to the desired thickness, with fluid removal occurring from both upper and lower surfaces (FIG. 1C). After compression, the hydrated collagen scaffolds were aseptically removed from the chamber and stored in sealed airtight sterile containers prior to testing.

Figure 2:
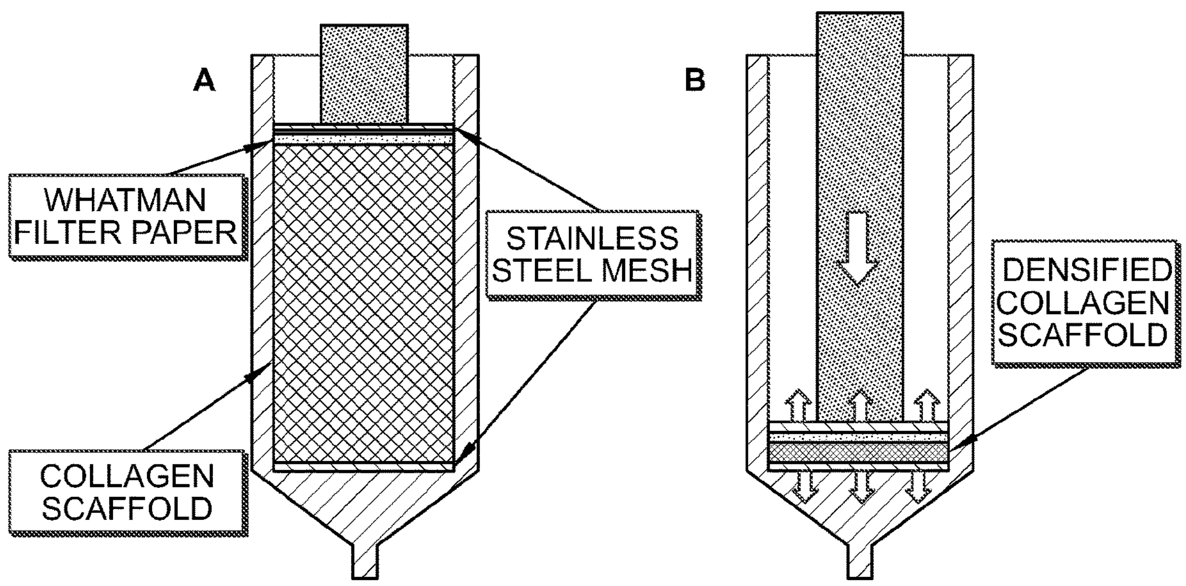
FIG. 2A shows a syringe compression device and associated densification/dehydration process in which a composite collagen scaffold is polymerized in the syringe system on top of a disk of stainless steel mesh. After polymerization, a piece of Whatman filter paper and a modified plunger were placed inside the syringe to compress the scaffold.
FIG. 2B shows that the plunger is compressed in the direction of the grey arrow to drive fluid out of the collagen scaffold in both directions (white arrows) to create a densified collagen scaffold.

Syringe Compression System:

Dual direction fluid removal during compression dehydration could also be achieved using a modified syringe system (FIG. 2). Syringes (6 cc Covidien Monoject, 1.2 cm diameter) were modified by removing the plunger and placing a disc of stainless-steel mesh (100×100 openings per 1"×1", 0.006" opening; McMaster-Carr, Douglasville, GA) inside the syringe, just before the tip. The rubber plunger from the syringe was modified by punching out the central region and attaching another disc of stainless-steel mesh over the created hole. Notches were also created in the edges of the rubber plunger in order to facilitate fluid flow and prevent air pressure build up when inserting the plunger into the syringe. The syringe tip was capped prior to addition of neutralized collagen solution to the body of the syringe, on top of the stainless steel mesh (the surface tension between the viscous collagen solution and the small grid of the mesh did not allow fluid to flow through the mesh). The syringes were sealed and incubated at 37° C. to allow collagen polymerization. After polymerization, the modified plunger was placed inside the syringe, along with a piece of Whatman filter paper to provide a cushion between the stainless-steel mesh and the composite collagen scaffold (in order to not imprint the mesh grip onto the scaffold during compression). The syringe was then loaded onto a syringe pump (Model NE-1600, New Era Pump Systems, Farmingdale, NY) for compression at a strain rate of 0.05% per second to the desired thickness.

Example 2

Quantification of Collagen Scaffold Thickness

Collagen scaffold thickness and uniformity were determined with a Mitutoyo 547-526S high-accuracy thickness gage (Aurora, IL; +/−5 μm accuracy). At least 5 measurements (n≥5) were made along a material sheet, including central and edge regions, and the associated average and standard deviation determined.

Example 3

Uniaxial Tensile Testing

Uniaxial tensile testing was performed in ambient air on dog-bone shaped material samples with a gauge length and width of 4 mm and 3 mm, respectively (n≥3). The average duration of mechanical testing from set up to completion was less than 10 seconds and sample dehydration was not observed. All samples were tested in uniaxial tension to failure at a strain rate of 40% per second (1.6 mm/min) using a servo-electric materials testing system (TestResources, Shakopee, MN) adapted with a 25 N load cell at a sampling rate of 32 Hz. Elastic modulus (ET) was calculated from the linear region of the stress strain curve. Ultimate stress (σU) represented peak stress experienced by the sample, and failure strain (εf) was the strain at which materials experienced total failure.

Example 4

Suture Retention Testing

Suture retention testing was performed in ambient air on 2×1 cm rectangular samples. To reproducibly place the suture in these samples, a suturing guide was used to place the suture along the long central axis of the sample with a bite distance of 2 mm. After throwing a single suture (5-0 Nylon, monofilament) through the sample, the guide was used to help type off the suture with two double square-knots, 2.5 cm from the edge of the sample. After the suture was tied in place, the sample was placed in a tensile testing machine (the same as used for tensile testing) by looping the suture over a hook held in the top grip of the machine and securing the bottom edge of the sample in the bottom grips. The suture was pulled at a rate of 10 mm/min to failure and the max load in newtons (N) was recorded as the suture retention strength.

Example 5

Hydrated Collagen Scaffolds

Figure 3:
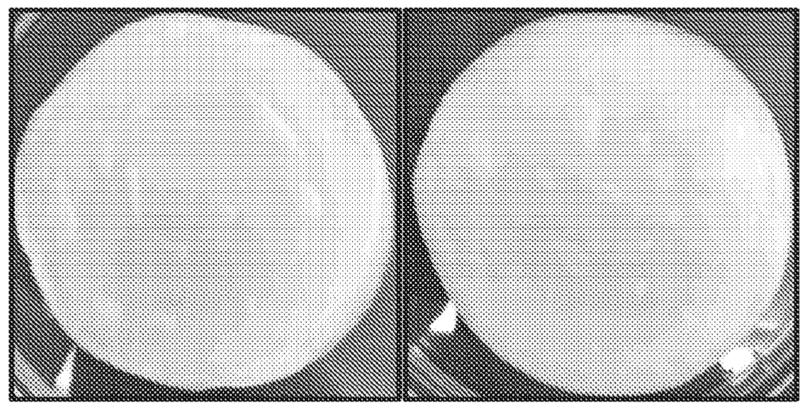
FIG. 3, left panel shows a photograph of a representative prototype collagen scaffold (6.3 cm diameter) prepared by compression dehydration using Formula 3.

Representative images of prototype hydrated collagen scaffolds prepared with the customized chamber compression system are shown in FIG. 3. Table 1 provides a summary of various scaffold formulations and associated properties.

TABLE 1

Summary of properties of various collagen scaffold prepared by compression dehydration.

| Formula | Total Collagen Content (mg) | Collagen Content (mg/cm$^3$) | Testing Conditions; Processing | Replicates | Mean Thickness (μm) | Elastic Modulus (MPa) | UTS (MPa) | Failure Strain (%) | Suture Retention Peak Load (N) |
|---|---|---|---|---|---|---|---|---|---|
| 1 | 315 | 188 ± 22 | in air; no processing | N = 4, n = 3 | 542 ± 55 | 7.79 ± 1.98 | 1.43 ± 0.44 | 30.6 ± 4.1 | 0.417 ± 0.034 |
| 2 | 235 | 338 ± 15 | in air; no processing | N = 1, n = 4 | 223 ± 10 | 19.6 ± 5.0 | 5.63 ± 0.85 | 45.0 ± 5.5 | ND |
| | | | hydrated; 24-hr PBS | N = 1, n = 3 | 231 ± 25 | 16.2 ± 4.3 | 3.01 ± 0.5 | 28.7 ± 4.7 | 0.453 ± 0.061 |
| 3 | 250 | 430 ± 47 | in air, no processing | N = 4, n = 3 | 188 ± 21 | 34.6 ± 8.4 | 6.88 ± 1.54 | 31.8 ± 5.0 | ND |
| | | | hydrated; 10-minute PBS | N = 1, n = 3 | 191 ± 19 | 28.0 ± 3.7 | 4.51 ± 0.56 | 22.3 ± 3.5 | 0.365 ± 0.049 |
| 4 | 500 | 505 ± 24 | in air, no processing | N = 4, n = 3 | 318 ± 15 | 35.3 ± 3.3 | 8.30 ± 0.54 | 37.6 ± 4.7 | ND |
| | | | hydrated; 10-minute PBS | N = 1, n = 3 | 307 ± 19 | 36.7 ± 5.3 | 5.89 ± 0.41 | 25.3 ± 4.7 | 0.833 ± 0.138 |

Example 6

Relationship Between Collagen Concentration and Collagen Scaffold Design

Figure 4A:
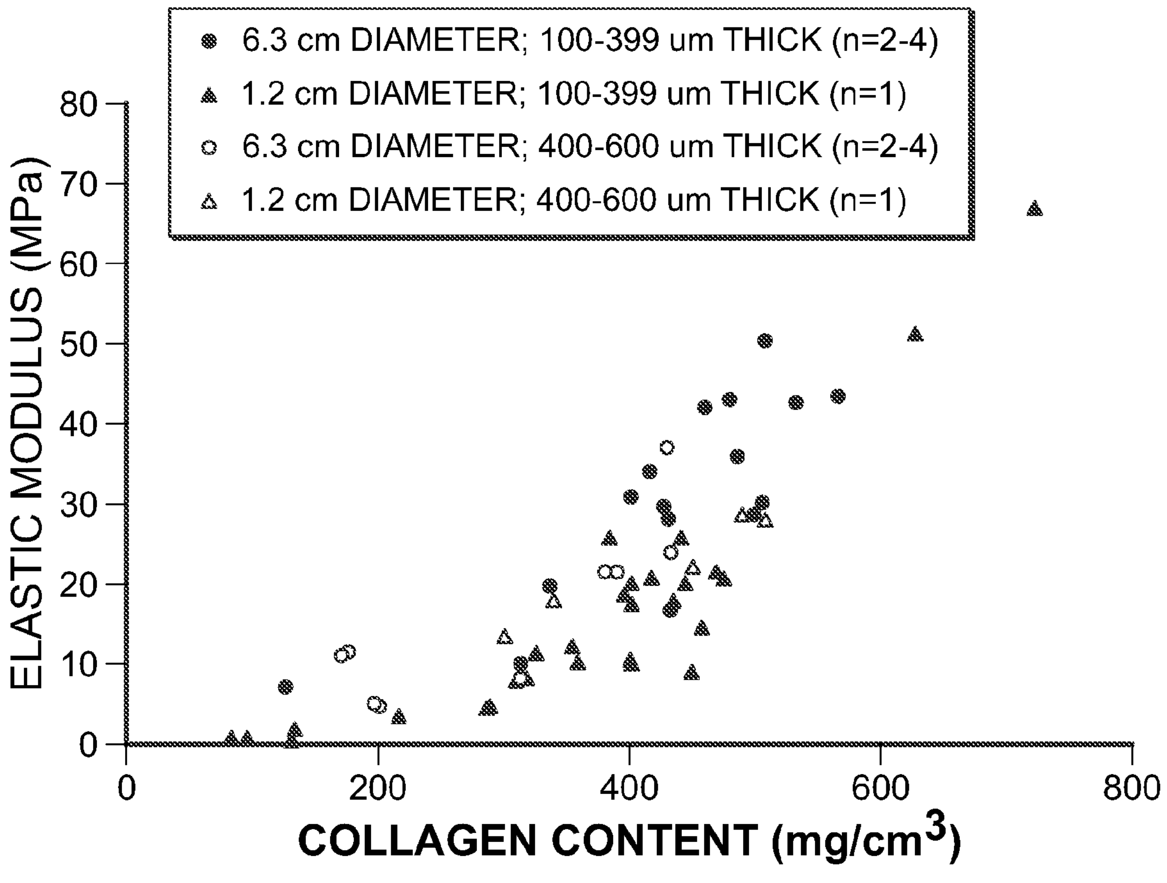
FIG. 4A shows the elastic modulus of collagen scaffolds.
Figure 4B:
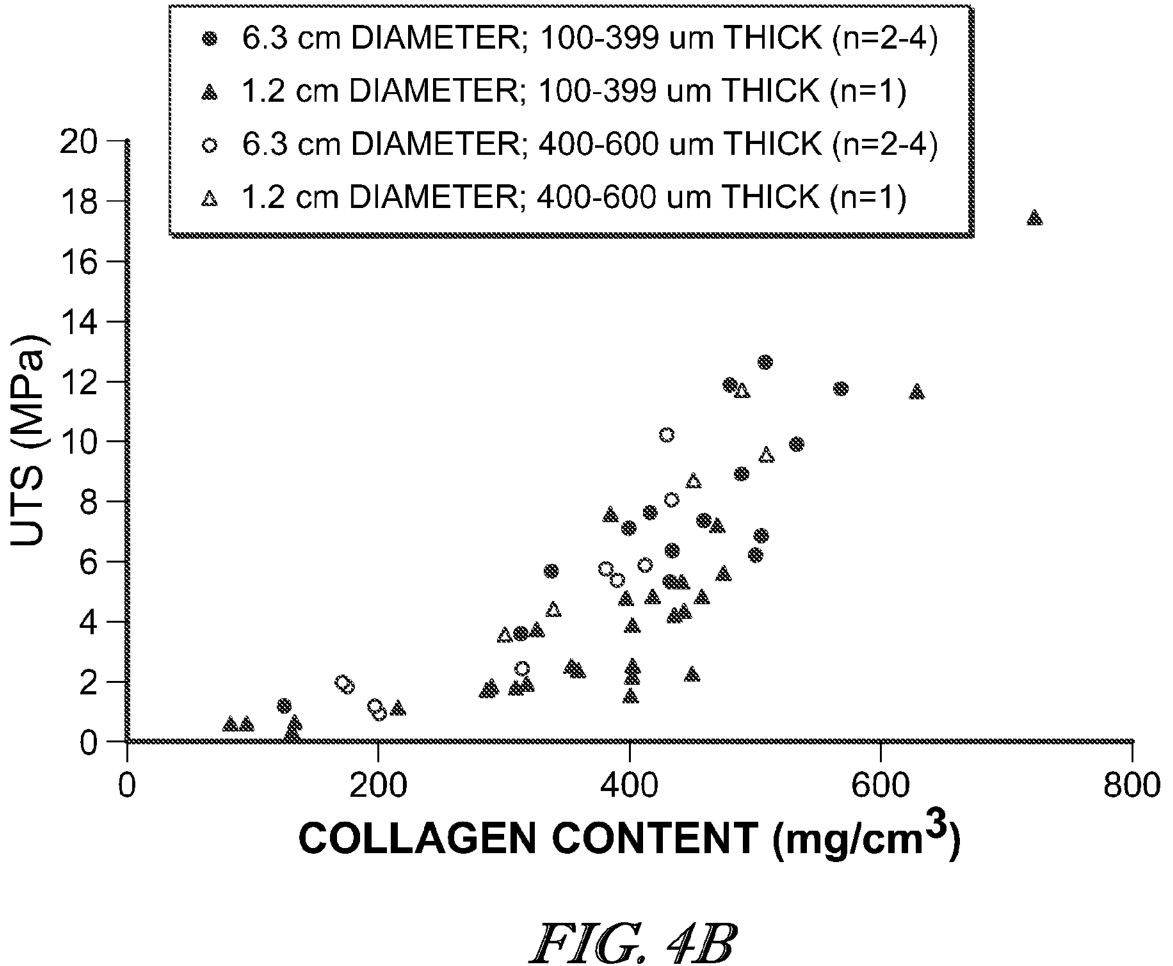
FIG. 4B shows the UTS of collagen scaffolds.
Figure 4C:
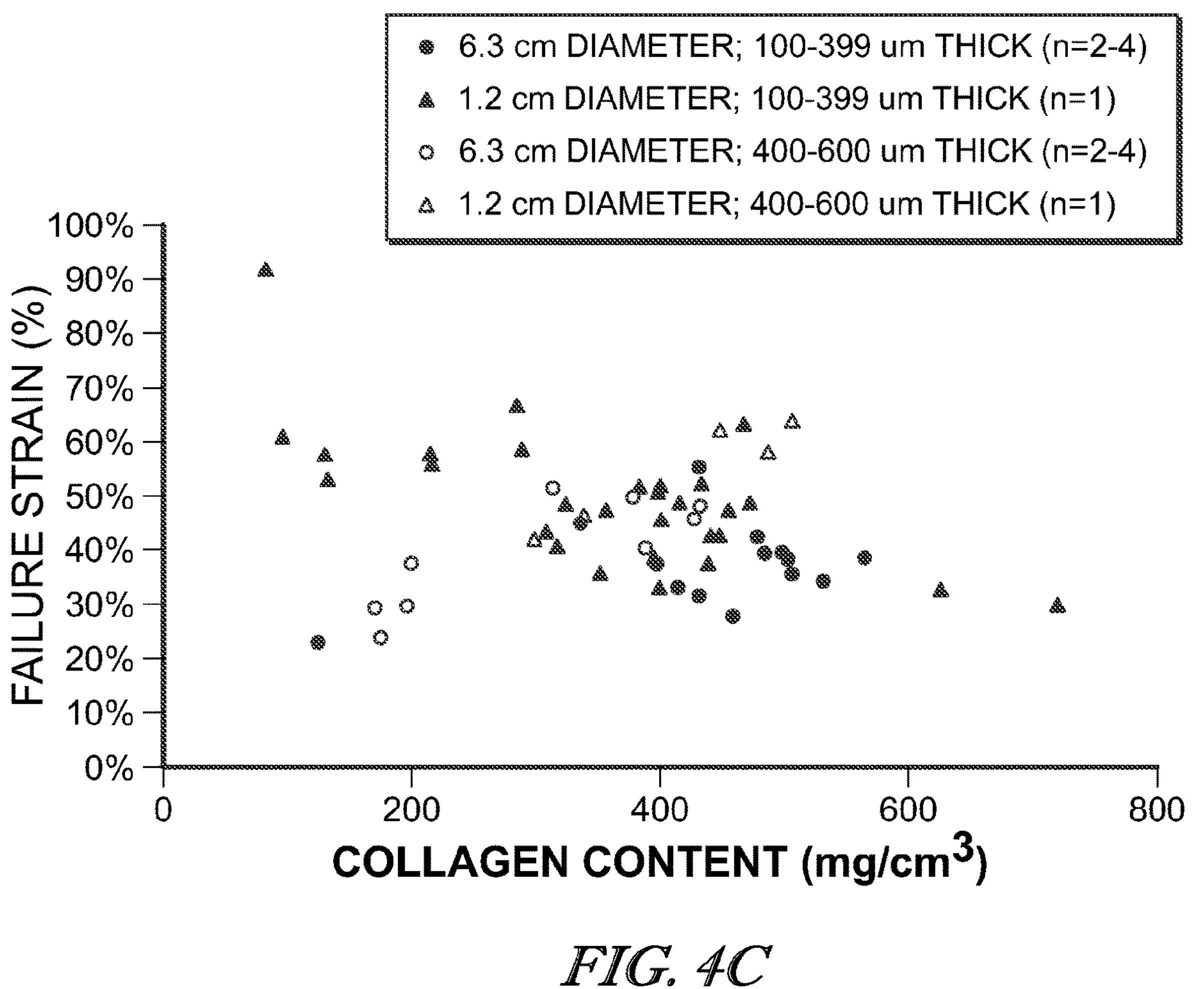
FIG. 4C shows failure strain as a function of collagen content.

To identify predictive relationships for customized collagen scaffold design, scaffolds were fabricated across a broad range of collagen concentrations (~100 mg/mL to 700 mg/mL) using either the chamber or syringe compression dehydration method. Scaffold mechanical properties, including elastic modulus, ultimate tensile strength (UTS), and failure strain were measured and plotted as a function of collagen content (FIG. 4).

Example 7

Collagen Scaffolds Made by Compression Dehydration

Figure 5:
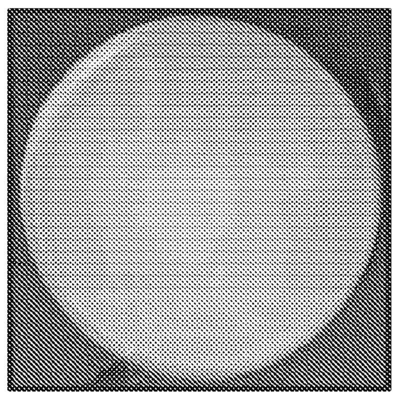
FIG. 5 shows an image of a prototype collagen scaffold (6.3 cm diameter) prepared with 500 mg total collagen content and processed with vacuum pressing followed by dehydrothermal (DHT) treatment at 90° C. The collagen scaffold was rehydrated in phosphate buffered saline.

To create desiccated collagen scaffolds, hydrated densified scaffolds were dehydrated to dryness using lyophilization or vacuum pressing. Prior to lyophilization and vacuum pressing, all scaffolds were rinsed extensively in water. For lyophilization, collagen scaffolds were secured in a frame that gripped the edges in order to prevent curling. Scaffolds were then flash frozen with liquid nitrogen and lyophilized overnight. For vacuum pressing, scaffolds were placed between two sheets of porous polyethylene foam and compressed under vacuum to until dry. In some cases, desiccated materials were further subjected to dehydrothermal (DHT) treatment, a process in which the material is heated under vacuum to further remove water molecules and create intermolecular crosslinks. For DHT treatment, desiccated scaffolds placed in a vacuum oven at a specified vacuum level and temperature for 24 hours. The vacuum was set to 50 mTorr and the temperature set to 60, 90, or 120° C. FIG. 5 shows an example of a desiccated collagen scaffold following rehydration in phosphate buffered saline. Table 2 summarizes properties of various collagen scaffold formulations prepared by compression dehydration and desiccation. In general, processing with DHT improved scaffold mechanical integrity (i.e., elastic modulus, UTS) and scaffold ability to maintain geometry (i.e., thickness) following rehydration. This was especially notable for scaffolds with high total collagen content (>500 mg; >500 mg/mL).

TABLE 2

Summary of properties of various collagen scaffolds prepared by compression dehydration followed by dessication via lyophilization or vacuum pressing. Thickness values for desiccated scaffolds prepared by vacuum pressing and lyophilization were 377 ± 25 μm and 604 ± 33 μm, respectively.

| Total Collagen Content (mg); Post Processing | Collagen Content (mg/cm$^3$) | Testing Conditions | Replicates | Mean Thickness (μm) | Elastic Modulus (MPa) | UTS (MPa) | Failure Strain (%) | Suture Retention Peak Load (N) |
|---|---|---|---|---|---|---|---|---|
| 500 mg; Vacuum Pressed | 197 ± 10 | in air, 24-hr PBS | N = 1, n = 3 | 902 ± 45 | 13.6 ± 3.0 | 2.54 ± 0.52 | 32.6 ± 2.9 | 0.982 ± 0.109 |
| 500 mg; Lyophilized | 195 ± 8 | in air, 24-hr PBS | N = 1, n = 3 | 910 ± 38 | 9.84 ± 5.77 | 2.18 ± 1.44 | 38.3 ± 4.2 | 0.927 ± 0.078 |
| 500 mg; Vacuum Pressed + DHT 60° C. | 401 ± 13 | in air, 24-hr PBS | N = 1, n = 3 | 441 ± 14 | 50.6 ± 4.2 | 8.22 ± 0.40 | 27.5 ± 3.5 | 0.757 ± 0.151 |
| 500 mg; Vacuum Pressed + DHT 90° C. | 434 ± 11 | in air, 24-hr PBS | N = 4, n = 3 | 399 ± 11 | 48.1 ± 2.7 | 8.48 ± 0.99 | 27.2 ± 4.9 | 0.917 ± 0.061 |
| | | in air, 20-day PBS | N = 4. n = 3 | 412 ± 10 | 41.4 ± 2.8 | 6.60 ± 0.89 | 21.2 ± 4.5 | ND |
| 500 mg; Vacuum Pressed + DHT 120° C. | 335 ± 17 | in air, 24-hr PBS | N = 1, n = 3 | 530 ± 27 | 40.7 ± 6.2 | 7.14 ± 1.15 | 28.6 ± 6.9 | 0.825 ± 0.090 |
| 500 mg; Lyophilized + DHT 60° C. | 244 ± 13 | in air, 24-hr PBS | N = 1, n = 3 | 726 ± 39 | 18.3 ± 3.6 | 3.44 ± 0.49 | 35.8 ± 1.6 | 0.846 ± 0.148 |
| 500 mg; Lyophilized + DHT 90° C. | 292 ± 11 | in air, 24-hr PBS | N = 1, n = 3 | 608 ± 24 | 15.9 ± 5.5 | 2.78 ± 1.00 | 33.9 ± 6.4 | 0.727 ± 0.040 |
| 500 mg; Lyophilized + DHT 120° C. | 305 ± 24 | in air, 24-hr PBS | N = 1, n = 3 | 582 ± 44 | 32.8 ± 1.6 | 4.54 ± 0.82 | 21.0 ± 5.6 | 0.746 ± 0.245 |

Example 8

Assessment of Collagen Scaffold Biocompatibility and Tissue Response Following Subcutaneous Implantation in Rats Preclinical Evaluation of Material Biocompatibility and Tissue Response:

Material biocompatibility and tissue response was assessed using an established rat subcutaneous implant model. This study involved adult male Sprague Dawley (Envigo, Indianapolis, Indiana) rats and all materials were evaluated in replicates of 10. All animals were housed under standard conditions (e.g., 25° C. temperature, 12 hour cycle light/dark) and provided a standard rat chow pellet diet and water ad libitum. At the time of the procedure, animals weighed between 272 g and 308 g. After induction of anesthesia, the animal's back was shaved, scrubbed with surgical scrub from hip to shoulder, and allowed to dry. Four lateral incisions, approximately 2 cm in length, were made on both sides of the back, parallel to the sagittal plane. The fascia was bluntly dissected to form a small pocket just lateral to the incision. Specimens (circular, 8 mm diameter) were implanted subcutaneously just beneath the cutaneous truncai muscle and the incision site closed with non-absorbable sutures. Sutures were removed 10-14 days following surgery. All animals were observed at a minimum of three times weekly and weighed weekly to assess both their physiological and mental states. After 60±2 days, the animals were euthanized and their dorsal side photographed after shaving. The subcutaneous tissue of the dorsum was then exposed, photographed, and radiographed. Each implant site and associated normal tissue was then collected and photographed prior to being divided in half for follow-up histopathological analysis and calcium analysis. Explanted tissue was fixed in 10% neutral buffered formalin, embedded in paraffin, sectioned, and stained with hematoxylin and eosin and von Kossa. A blinded gross examination of all implant sites and associated materials was conducted immediately upon surgical dissection/exposure and following preparation for histopathological analysis. Specimens were scored based on the level of tissue reaction and tissue integration as summarized below. Histopathological analysis of explants was performed by a blinded pathologist.

Tissue Reaction (Assessed Immediately Upon Surgical Dissection/Exposure)

0=None
1=Marginal
2=Minimal
3=Moderate
4=Extensive

Tissue Integration (Assessed During Sample Preparation for Calcium Analysis)

0=None
1=Marginal
2=Minimal
3=Moderate
4=Extensive

Figure 6:
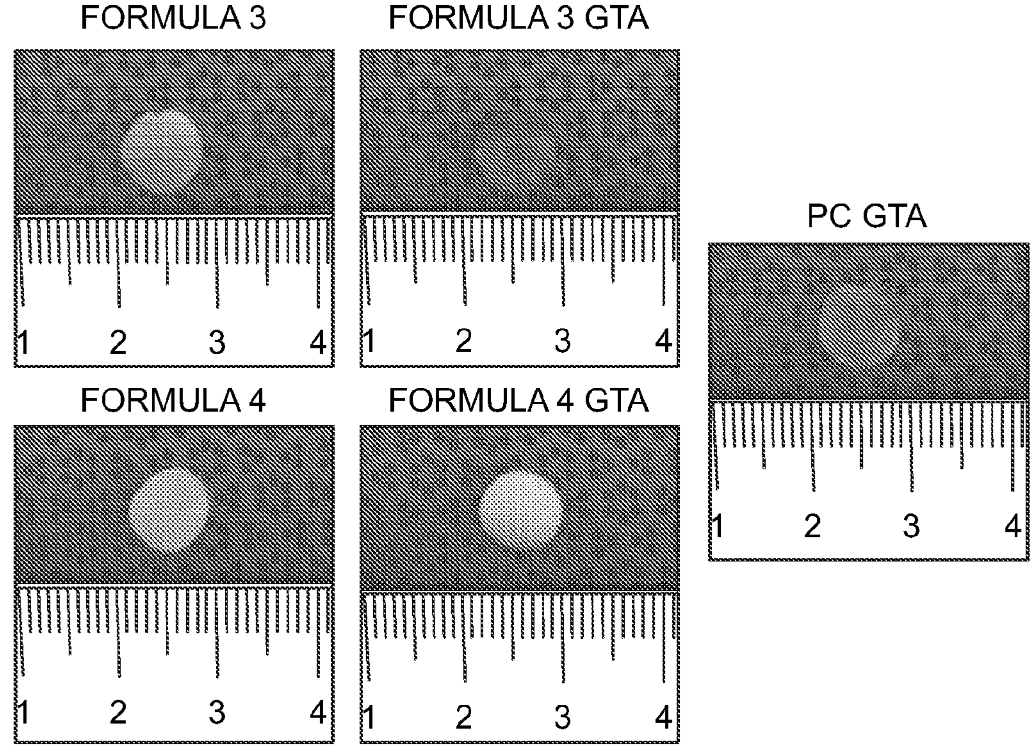
FIG. 6 shows photographs of materials prior to subcutaneous implantation in rats, including Formula 3 and 4 collagen scaffolds in the absence and presence of glutaraldehyde (GTA) treatment and glutaraldehyde-treated pericardium (PC GTA).
Figure 7:
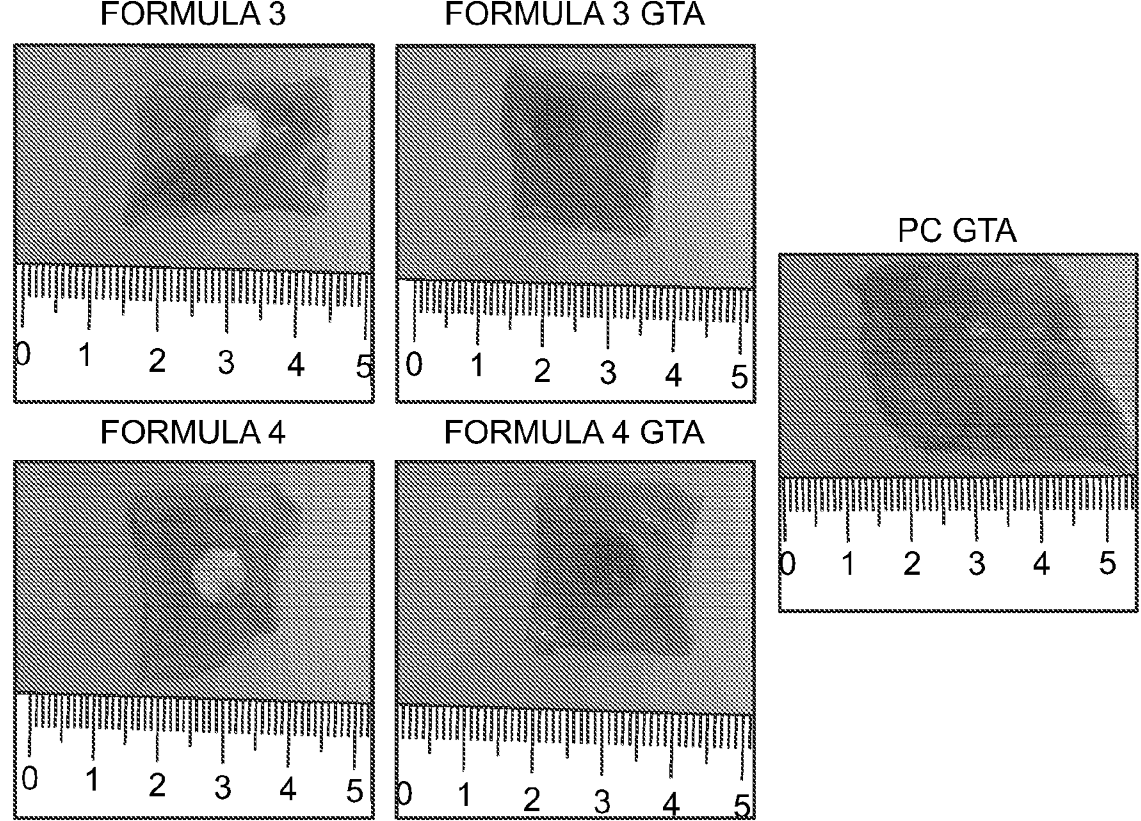
FIG. 7 shows photographs of material explants 60 days following subcutaneous implantation in rats, including Formula 3 and 4 collagen scaffolds in the absence and presence of glutaraldehyde (GTA) treatment and glutaraldehyde-treated pericardium (PC GTA).
Figure 8:
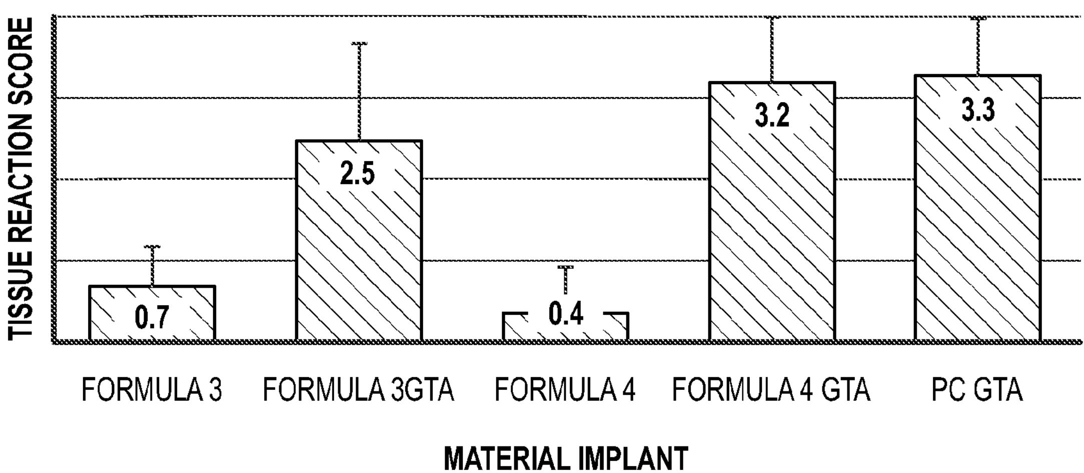
FIG. 8 shows a summary of semi-quantitative scores (mean±SD; n=10) for tissue reaction and tissue integration as determined via gross observation of material explants 60 days following subcutaneous implantation in rats.
Figure 8:
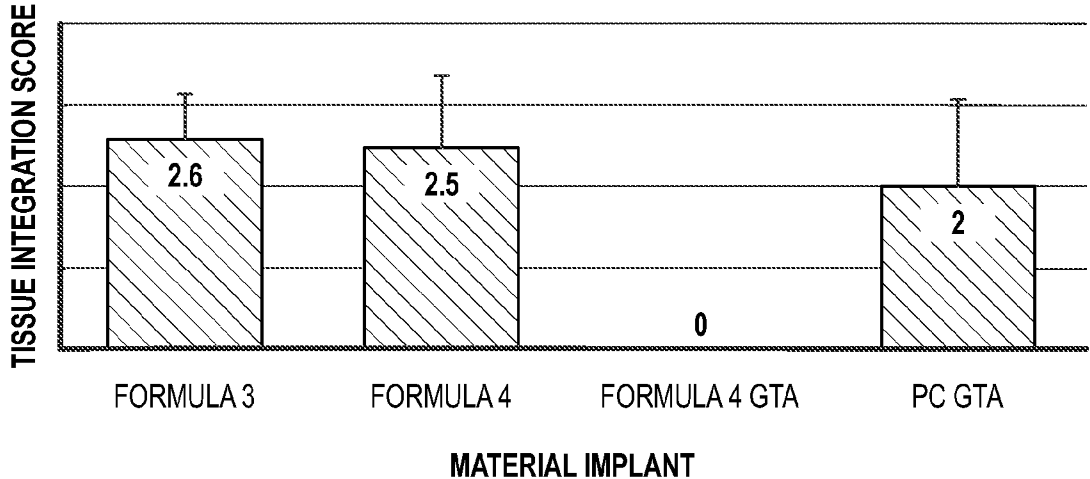
Figure 9:
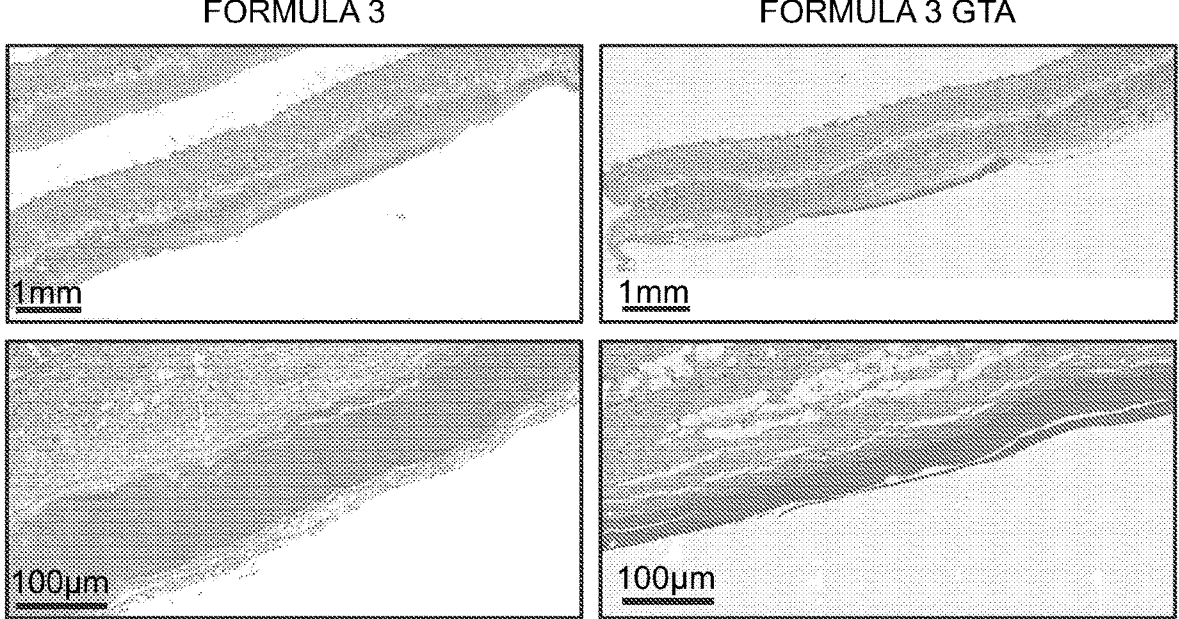
FIG. 9 shows low (upper) and high (lower) magnification images of histological cross-sections (hematoxylin & eosin stained) of skin explant and associated collagen scaffold (Formula 3) in the absence and presence of glutaraldehyde (GTA) treatment.
Figure 10:
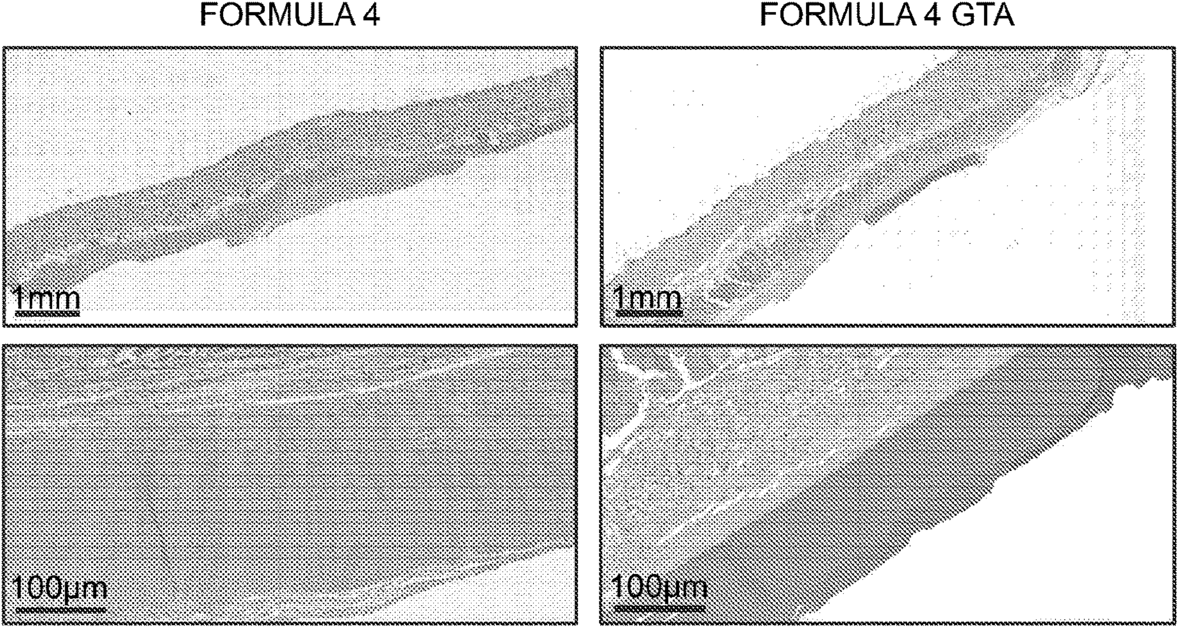
FIG. 10 shows low (upper) and high (lower) magnification images of histological cross-sections (hematoxylin & eosin stained) of skin explant and associated collagen scaffold (Formula 4) in the absence and presence of glutaraldehyde (GTA) treatment.
Figure 11:
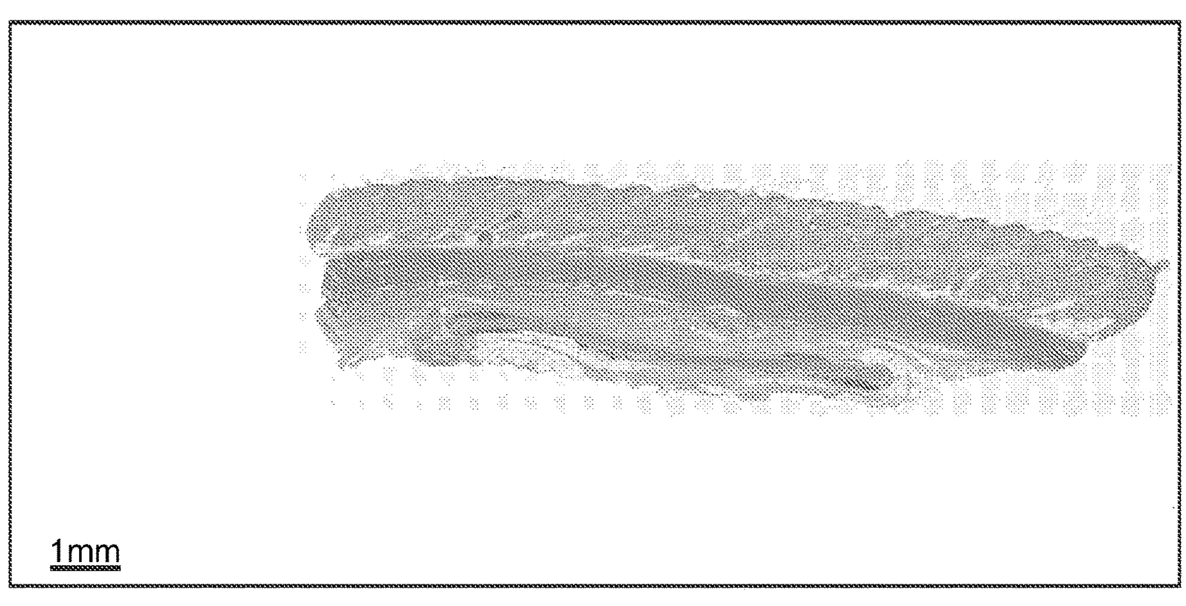
FIG. 11 shows low (upper) and high (lower) magnification images of histological cross-sections (hematoxylin & eosin stained) of skin explant and associated glutaraldehyde-treated pericardium (PC GTA).
Figure 11:
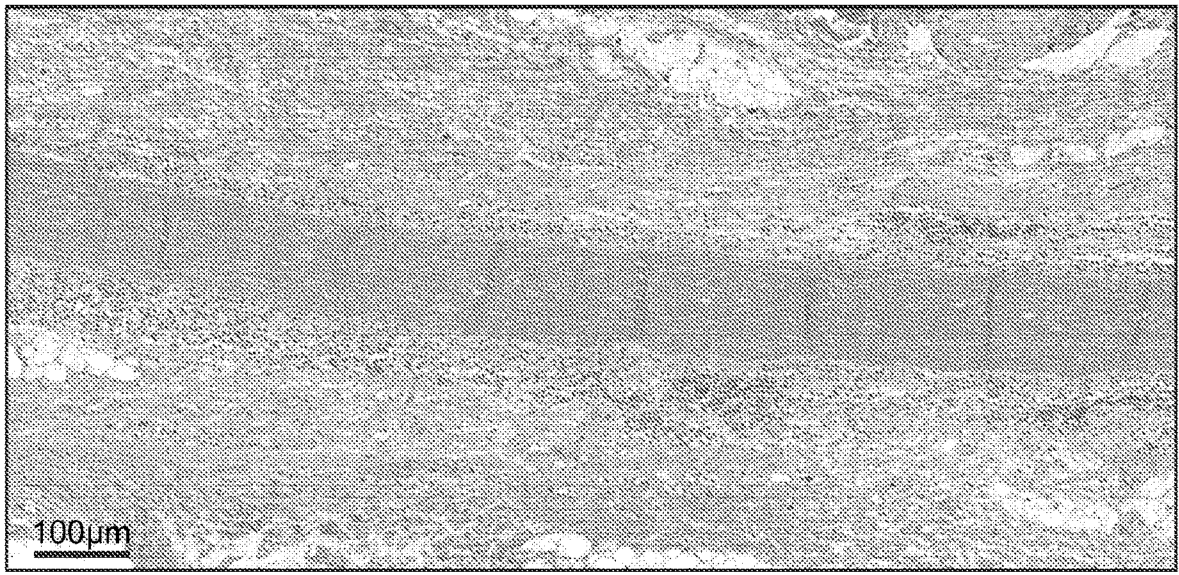

Results:

The biocompatibility and tissue response of collagen scaffolds, specifically Formula 3 and 4 (as originally described in Example 1, Table 1), prepared without and with glutaraldehyde treatment, were evaluated in an established 60-day rat subcutaneous implant model, with glutaraldehyde-treated pericardium serving as a reference material. Photographs of representative materials for each group prior to implantation are shown in FIG. 6, with Table 3 providing a summary of materials and mechanical properties. Glutaraldehyde treatment of collagen scaffolds resulted in i) increased elastic modulus and UTS, ii) modestly increased suture retention, and iii) decreased failure strain. Formula 3 and 4 collagen scaffolds appeared white in color, while materials treated with glutaraldehyde were various shades of tan. Representative images of skin explants with associated implant materials 60±2 days following implantation are provided in FIG. 7. Differences in the extent of tissue reaction (i.e., fibrous tissue associated with implant) and tissue integration (i.e., adhesion between material implant and surrounding host tissue) were observed grossly and scored, with results summarized in FIG. 8. In general, all materials, except untreated Formula 3 and 4, displayed various levels of a foreign body reaction with notable fibrous tissue overgrowth. Histopathological analysis revealed that Formula 3 and 4 scaffolds appeared as homogenous materials with linearly oriented fibers, similar to native collagen. For these materials the pattern of inflammation was universally mild and the fibrotic response was generally minimal with smooth transition from implant to surrounding tissues (FIGS. 9 and 10). The inflammatory response to glutaraldehyde treated collagen scaffolds was also mild (FIGS. 9 and 10); however, a moderately mature fibrotic response was typically observed around the implant. Consistent with other published studies, glutaraldehyde treated pericardium appeared as coarse fibrous material with linearly-oriented fibers, with a moderate inflammatory response which was consistently circumferential (FIG. 11). Lymphocytes and other inflammatory cells were often observed infiltrating between fibrils and a moderate fibrotic response was always present. There was no detectable calcification associated with any of the materials.

TABLE 3

Summary of properties of collagen scaffolds and reference materials evaluated for biocompatibility and tissue response in an established rat subcutaneous implant model.

| Material | Total Collagen Content (mg) | Collagen Content (mg/cm$^3$) | Testing Conditions; Processing | Replicates | Mean Thickness (μm) | Elastic Modulus (MPa) | UTS (MPa) | Failure Strain (%) | Suture Retention Peak Load (N) |
|---|---|---|---|---|---|---|---|---|---|
| Collagen Formula 3 | 250 | 430 ± 47 | in air, no processing | N = 4, n = 3 | 188 ± 21 | 34.6 ± 8.4 | 6.88 ± 1.54 | 31.8 ± 5.0 | ND |
| | | | hydrated; 10-minute PBS | N = 1, n = 3 | 191 ± 19 | 28.0 ± 3.7 | 4.51 ± 0.56 | 22.3 ± 3.5 | 0.365 ± 0.049 |
| Collagen Formula 3 GTA | 250 | | hydrated; 10-minute PBS | N = 1, n = 3 | 167 ± 9 | 129 ± 7.4 | 11.98 ± 3.58 | 9.3 ± 2.1 | 0.167 ± 0.09 |
| Collagen Scaffold Formula 4 | 500 | 505 ± 24 | in air, no processing | N = 4, n = 3 | 318 ± 15 | 35.3 ± 3.3 | 8.30 ± 0.54 | 37.6 ± 4.7 | 0.61 |
| | | | hydrated; 10-minute PBS | N = 1, n = 3 | 307 ± 19 | 36.7 ± 5.3 | 5.89 ± 0.41 | 25.3 ± 4.7 | 0.833 ± 0.138 |
| Collagen Scaffold Formula 4 GTA | 500 | | hydrated; 10-minute PBS | N = 1, n = 3 | 297 ± 22 | 174.4 ± 49.8 | 17.82 ± 8.33 | 13.7 ± 1.5 | 1.073 ± 0.206 |
| PC GTA | NA | NA | hydrated | N = 2, n = 3 | 239 ± 25 | 45.4 ± 12.5 | 17.4 ± 4.8 | 66.8 ± 25.3 | 3.28 ± 0.59 |

Example 9

Collagen Polymerization

The composition of the engineered collagen scaffolds for polymerization can include type I oligomeric collagen in 0.01N hydrochloric acid, which has been neutralized by mixing in a 10:1 ratio with the 10× buffer provided below. Glucose can be included if cells are to be included. The combination of collagen solution in dilute acid with this 10× buffer induces a fibril-forming reaction. This composition can be added to a chamber compression system, as described herein, and can be incubated at 37° C. to induce collagen polymerization.

(10× Phosphate Buffered Saline)

1.37 M NaCl
0.027 M KCl
0.081 M $Na_2HPO_4$
0.015 M $KH_2PO_4$
0.1N NaOH
55.6 mM Glucose

What is claimed is:

1. A non-collapsible and/or non-expandable collagen scaffold comprising oligomeric collagen formed by compressing a polymerized oligomeric collagen scaffold into a defined shape having a thickness of about 0.005 mm to about 3 mm, a collagen density of about 50 to about 1000 mg/$cm^3$ and an elastic modulus of about 0.5 MPa to about 200 MPa, wherein said compressed polymerized oligomeric collagen scaffold will not swell or collapse when lyophilized or rehydrated.

2. The non-collapsible and/or non-expandable collagen scaffold of claim 1, wherein the non-collapsible and/or non-expandable collagen scaffold has a suture retention load of about 0.1 N to about 4 N.

3. The non-collapsible and/or non-expandable collagen scaffold of claim 1, wherein the non-collapsible and/or non-expandable collagen scaffold has an ultimate tensile strength of about 1 MPa to about 25 MPa.

4. The non-collapsible and/or non-expandable collagen scaffold of claim 1, wherein the polymerized oligomeric collagen scaffold is compressed into a defined shape selected from the group consisting of a sphere, a tube and a sheet.

5. The non-collapsible and/or non-expandable collagen scaffold of claim 1, wherein the compression is confined compression.

6. A method of treating a patient to replace, restore, or regenerate a damaged or a dysfunctional tissue, the method comprising implanting into the patient a medical graft comprising the non-collapsible and/or non-expandable collagen scaffold of claim 1.

7. The method of claim 6, wherein the medical graft is for the regeneration, restoration, or replacement of damaged or dysfunctional pericardium.

8. The method of claim 6, wherein the medical graft is for the regeneration, restoration, or replacement of damaged or dysfunctional heart valve tissue.

9. The method of claim 6, wherein the medical graft is for the regeneration, restoration, or replacement of damaged or dysfunctional skin.

10. The method of claim 8, wherein the heart valve tissue is aortic heart valve tissue or pulmonic valve tissue.

11. A non-collapsible and/or non-expandable oligomeric collagen scaffold, wherein the non-collapsible and/or non-expandable oligomeric collagen scaffold is formed from Type I oligomeric collagen that has been polymerized in the absence of an added crosslinking agent and compressed into a defined shape having a thickness of about 0.005 mm to about 3 mm, and a collagen density of about 50 to about 1000 mg/$cm^3$.

12. The oligomeric collagen scaffold of claim 11, having an elastic modulus of about 0.5 MPa to about 200 MPa.

13. The oligomeric collagen scaffold of claim 11, wherein the collagen density is about 50 to about 700 mg/$cm^3$.

14. The oligomeric collagen scaffold of claim 11, formed by heating and subjecting the polymerized oligomeric collagen to a vacuum to compress the polymerized oligomeric collagen into a defined shape having a thickness of from 0.005 mm to 3 mm, and a collagen density of 100 to 700 mg/$cm^3$.

15. The oligomeric collagen scaffold of claim 11, having a thickness of about 0.1 mm to about 2 mm, and a collagen density of about 50 to about 700 mg/$cm^3$.

16. The oligomeric collagen scaffold of claim 11, having a thickness of about 0.1 mm to about 1 mm, and a collagen density of about 50 to about 700 mg/$cm^3$.

17. The oligomeric collagen scaffold of claim 11, further comprising cells.

18. The oligomeric collagen scaffold of claim 11, formed by subjecting the polymerized Type I oligomeric collagen scaffold to confined compression, where said defined shape is selected from the group consisting of a sphere, a tube and a sheet, and wherein said compressed polymerized oligomeric collagen scaffold will not swell or collapse when lyophilized or rehydrated.

* * * * *